US012807923B2

(12) United States Patent
Kramme et al.

(10) Patent No.: US 12,807,923 B2
(45) Date of Patent: Nov. 24, 2026

(54) APPARATUS AND METHOD FOR INDUCING HUMAN OOCYTE MATURATION IN VITRO

(71) Applicant: Gameto, Inc., New York, NY (US)

(72) Inventors: Christian Kramme, New York, NY (US); Dina Radenkovic, New York, NY (US); Martin Varsavsky, New York, NY (US); Klaus E. Wiemer, New York, NY (US)

(73) Assignee: Gameto, Inc., Austin, TX (US)

( * ) Notice: Subject to any disclaimer, the term of this patent is extended or adjusted under 35 U.S.C. 154(b) by 0 days.

(21) Appl. No.: 18/371,694

(22) Filed: Sep. 22, 2023

(65) Prior Publication Data

US 2024/0166992 A1 May 23, 2024

Related U.S. Application Data

(63) Continuation of application No. 17/846,725, filed on Jun. 22, 2022, now Pat. No. 11,802,268.

(51) Int. Cl.
*C12N 5/075* (2010.01)

(52) U.S. Cl.
CPC .................................. *C12N 5/0609* (2013.01)

(58) Field of Classification Search
None
See application file for complete search history.

(56) References Cited

U.S. PATENT DOCUMENTS

| | | | |
|---|---|---|---|
| 10,392,601 B2 | 8/2019 | Romero et al. | |
| 10,792,311 B2 | 10/2020 | Cheng et al. | |
| 11,744,920 B1 | 9/2023 | Radenkovic et al. | |
| 11,802,268 B1 | 10/2023 | Kramme et al. | |
| 2006/0194235 A1 | 8/2006 | Chen et al. | |
| 2013/0089870 A1 | 4/2013 | Yamanaka et al. | |
| 2015/0359822 A1 | 12/2015 | Atwood | |
| 2016/0001051 A1 | 1/2016 | Kumar et al. | |
| 2016/0237402 A1 | 8/2016 | Tilly et al. | |
| 2017/0290890 A1 | 10/2017 | Cheng et al. | |
| 2018/0015127 A1 | 1/2018 | Ichim et al. | |
| 2018/0251729 A1* | 9/2018 | Obata | C12N 5/0609 |
| 2019/0288915 A1 | 9/2019 | Denyer et al. | |
| 2020/0279635 A1 | 9/2020 | Letterie et al. | |
| 2021/0261922 A1 | 8/2021 | Nagamatsu et al. | |
| 2021/0290632 A1 | 9/2021 | Freedman et al. | |
| 2022/0010270 A1 | 1/2022 | Sivanandane et al. | |
| 2022/0399091 A1 | 12/2022 | Loewke et al. | |

FOREIGN PATENT DOCUMENTS

| | | |
|---|---|---|
| WO | WO-2009/138855 A2 | 11/2009 |
| WO | WO-2010003020 A1 | 1/2010 |
| WO | WO-2012/121874 A1 | 9/2012 |
| WO | WO-2016094970 A1 | 6/2016 |
| WO | WO-2017047799 A1 | 3/2017 |
| WO | WO-2020/072977 A1 | 4/2020 |
| WO | WO-2020/225085 A1 | 11/2020 |
| WO | WO-2023/192934 A2 | 10/2023 |
| WO | WO-2023/250101 A1 | 12/2023 |
| WO | WO-2024/206245 A1 | 10/2024 |

OTHER PUBLICATIONS

Dandekar et al. "Maturation of immature oocytes by coculture with granulosa cells." Fertility and Sterility 55.1 (1991): 95-99. (Year: 1991).*

Combelles et al. "In vitro maturation of human oocytes and cumulus cells using a co-culture three-dimensional collagen gel system." Human Reproduction 20.5 (2005): 1349-1358. (Year: 2005).*

Hofmann et al. "High-dose follicle-stimulating hormone (FSH) ovarian stimulation in low-responder patients for in vitro fertilization." Journal of in vitro Fertilization and Embryo Transfer 6 (1989): 285-289. (Year: 1989).*

Fatemi et al. "Dose adjustment of follicle-stimulating hormone (FSH) during ovarian stimulation as part of medically-assisted reproduction in clinical studies: a systematic review covering 10 years (2007-2017)." Reproductive Biology and Endocrinology 19.1 (2021): 68. (Year: 2021).*

Virant-Klun et al. "Human oocyte maturation in vitro is improved by co-culture with cumulus cells from mature oocytes." Reproductive Biomedicine Online 36.5 (2018): 508-523. (Year: 2018).*

Fadini, Rubens, et al. "Oocyte in vitro maturation in normo-ovulatory women." Fertility and sterility 99.5 (2013): 1162-1169. (Year: 2013).*

De Vos et al. "Clinical outcome of non-hCG-primed oocyte in vitro maturation treatment in patients with polycystic ovaries and polycystic ovary syndrome." Fertility and sterility 96.4 (2011): 860-864. (Year: 2011).*

Silvestris, Erica, et al. "In vitro generation of oocytes from ovarian stem cells (OSCs): in search of major evidence." International journal of molecular sciences 20.24 (2019): 6225. (Year: 2019).*

Pongsuthirak et al., "Comparison of Blastocyst and Sage Media for In Vitro Maturation of Human Immature Oocytes," Reprod Sci. 22(3):343-346 (Mar. 2015).

Zhang et al., "A flexible short protocol in women with poor ovarian response over 40 years old," J Ovarian Res. 14(1):1-8 (Jan. 2021).

Virant-Klun et al., "Human oocyte maturation in vitro is improved by co-culture with cumulus cells from mature oocytes," Reprod Biomed Online. 36(5):508-523 (May 2018).

(Continued)

*Primary Examiner* — Emily A Cordas
(74) *Attorney, Agent, or Firm* — Clark & Elbing LLP

(57) ABSTRACT

An apparatus and method for inducing human oocyte maturation in vitro, the apparatus including: a computing device, wherein the computing device includes at least a processor; and a memory communicatively connected to the at least processor, the memory containing instructions configuring the at least processor to receive first biological sample data from a first biological sample relating to a user; assign the user to a stimulation protocol as a function of the first biological sample; receive second biological sample data from a second biological sample relating to the user wherein the second biological sample comprises at least an immature oocyte; receive culture data relating the second biological sample; and assign the second biological sample a scoring metric as a function of the culture data of the second biological sample.

21 Claims, 9 Drawing Sheets

(56) References Cited

OTHER PUBLICATIONS

Devroey et al., "Clinical outcome of a pilot efficacy study on recombinant human follicle-stimulating hormone (Org 32489) combined with various gonadotrophin-releasing hormone agonist regimens," Hum Reprod. 9(6):1064-1069 (Jun. 1994).
Prasannan et al., "Iot based Device for Fertility Monitoring," 2020 5th International Conference on Communication and Electronics Systems (ICCES), June 10-12, Coimbatore, India. (2020) (5 pages).
Dandekar et al., "Maturation of immature oocytes by coculture with granulosa cells," Fertil Steril. 55(1):95-9 (Jan. 1991).
Pongsuthirak et al., "Comparison of Medicult and Sage Media for In Vitro Maturation of Immature Oocytes Obtained during Cesarean Deliveries," JFIV Reprod Med Genet. 3(1): 1-4 (Dec. 2014) (5 pages).
Lonergan et al., "Maturation of Oocytes in Vitro," Annu Rev Anim Biosci. 4:255-268 (2016) (16 pages).
Lazzaroni-Tealdi et al. "Oocyte Scoring Enhances Embryo-Scoring in Predicting Pregnancy Chances with IVF Where It Counts Most." PLoS One. 10(12):e0143632 (Dec. 2015) (19 pages).
Torre et al., "In vitro maturation of human oocytes in a follicle-mimicking three-dimensional coculture," Fertil Steril. 86(3):572-6 (Sep. 2006).
International Search Report and Written Opinion for PCT/US2023/026012, dated Nov. 27, 2023 (24 pages).
Johnson et al., "Effect of human granulosa cell co-culture using standard culture media on the maturation and fertilization potential of immature human oocytes," Fertil Steril. 90(5):1674-9 (Nov. 2008).
Trounson et al., "In vitro maturation and the fertilization and developmental competence of oocytes recovered from untreated polycystic ovarian patients," Fertil Steril. 62(2):353-62 (Aug. 1994).
Schramm et al., "Granulosa cells from follicle stimulating hormone-primed monkeys enhance the developmental competence of in-vitro-matured oocytes from non-stimulated rhesus monkeys," Hum Rprod. 11(8):1698-702 (Aug. 1986).
Kopper et al., "An organoid platform for ovarian cancer captures intra- and interpatient heterogeneity," Nat Med. 25(5):838-849 (May 2019) (27 pages).
Sittadjody et al., "Encapsulation of Mesenchymal Stem Cells in 3D Ovarian Cell Constructs Promotes Stable and Long-Term Hormone Secretion with Improved Physiological Outcomes in a Syngeneic Rat Model," Ann Biomed Eng. 48(3):1058-1070 (Mar. 2020).
Lukonin et al., "Organoids in image-based phenotypic chemical screens," Exp Mol Med. 53(10):1495-1502 (Oct. 2021).
Ng et al., "A comprehensive library of human transcription factors for cell fate engineering," Nat Biotechnol. 39(4):510-519 (Apr. 2021) (18 pages).
Singh et al., "Gonadotropins as pharmacological agents in assisted reproductive technology and polycystic ovary syndrome," Trends Endocrinol Metab. 34(4):194-215 (Apr. 2023).
International Search Report and Written Opinion for PCT/US2023/030167, dated Dec. 1, 2023 (17 pages).
Hillier et al., "Role of androgens in follicle maturation and atresia," Baillieres Clin Obstet Gynaecol. 11(2):249-60 (Jun. 1997).
Smela et al., "Directed differentiation of human iPSCs to functional ovarian granulosa-like cells via transcription factor overexpression," Elife. 12:e83291 (Feb. 2023) (19 pages).
Velletri et al., "Single cell-derived spheroids capture the self-renewing subpopulations of metastatic ovarian cancer," Cell Death Differ. 29(3):614-626 (Mar. 2022).
Kramme et al., "An integrated pipeline for mammalian genetic screening," Cell Rep Methods. 1(6):100082 (Sep. 2021) (20 pages).
Yoon et al., "Integration of Genomic Profiling an Organoid Development in Precision Oncology," Int J Mol Sci. 23(1):216 (Dec. 2021) (15 pages).
Kobayashi et al., "Principles of early human development and germ cell program from conserved model systems," Nature. 546(7658):416-420 (Jun. 2017).
Heidari-Khoei et al., "Organoid technology in female reproductive biomedicine," Reprod Biol Endocrinol. 18(1):64 (Jun. 2020) (19 pages).
Stejskalová et al., "In vitro modelling of the physiological and diseased female reproductive system," Acta Biomater. 132:288-312 (Sep. 2021).
Lipskind et al., "An Embryonic and Induced Pluripotent Stem Cell Model for Ovarian Granulosa Cell Development and Steroidogenesis," 25(5):712-726 (Aug. 2017).
Lan et al., "Differentiation of Human Embryonic Stem Cells Into Functional Ovarian Granulosa-like Cells," J Clin Endocrinol Metab. 98(9):3713-23.
Smela et al., "Directed Differentiation of Human iPSCs to Functional Ovarian Granulosa-Like Cells via Transcription Factor Overexpression," bioRxviv. doi: https://doi.org/10.1101/2022.07.04.498717 (Jul. 2022) (21 pages).
N A Ho et al., "The effectiveness and safety of in vitro maturation of oocytes versus in vitro fertilization in women with a high antral follicle count," Hum Reprod. 34(6):1055-1064 (Jun. 2019) (11 pages).
Fadini et al., "Effect of different gonadotrophin priming on IVM of oocytes from women with normal ovaries: a prospective randomized study," Reprod Biomed Online. 19(3):343-351 (Sep. 2009) (10 pages).
Abdel-Ghani et al., "In vitro maturation of canine oocytes co-cultured with bovine and canine granulosa cell monolayers," Theriogenology. 77(2):347-355 (Jan. 2012).
Cakmak et al., "Metaphase II (MII) oocytes obtained at different time points in the same in vitro fertilization cycle," J Assist Reprod Genet. 29:1203-1205 (Sep. 2012).
Chen et al., "Autologous transplantation of thecal stem cells restores ovarian function in nonhuman primates," Cell Discov. 7(1):75 (Aug. 2021) (16 pages).
Communication pursuant to Rule 114(2) EPC for European Patent Application No. 23741889.2, dated Oct. 1, 2025 (3 pages).
Corfman et al., "A novel ovarian stimulation protocol for use with the assisted reproductive technologies," Fertil Steril. 60(5):864-70 (Nov. 1993).
De Roo et al., "In Vitro Maturation of Oocytes Retrieved from Ovarian Tissue: Outcomes from Current Approaches and Future Perspectives," J Clin Med. 10:4680 (Oct. 2021) (15 Pages).
Motlik et al., "Co-culture with pig membrana granulose cells modulates the activity of CDk1 and MAP kinase in maturing cattle oocytes," Zygote. 4(3): 247-256. (Sep. 1996).
Park et al., "Ovarian-cell-like cells from skin stem cells restored estradiol production and estrus cycling in ovariectomized mice," Stem Cells Dev. 23(14):1647-1658 (Jul. 2014).
Response to Communication pursuant to Rule 114(2) EPC for European Patent Application No. 23741889.2, dated Oct. 16, 2025 (18 pages).
Sittadjody et al., "In vivo transplantation of 3D encapsulated ovarian constructs in rats corrects abnormalities of ovarian failure," Nat Commun. 8(1):1858 (Dec. 2017) (13 pages).
Turathum et al., "The Function of Cumulus Cells in Oocyte Growth and Maturation and in Subsequent Ovulation and Fertilization," Cells. 10(9):2292 (Sep. 2021) (18 Pages).
Yamashiro et al., "Generation of human oogonia from induced pluripotent stem cells in vitro," Science. 362(6512):356-360 (Oct. 2018) (47 pages).
Yoon et al., "Hormone autocrination by vascularized hydrogel delivery of ovary spheroids to rescue ovarian dysfunctions," Sci Adv. 7(18):eabe8873 (Apr. 2021) (15 pages).
Yoshino et al., "Generation of ovarian follicles from mouse pluripotent stem cells," Science. 373(6552):eabe0237 (Jul. 2021).
Vuong et al., "Live births after oocyte in vitro maturation with a prematuration step in women with polycystic ovary syndrome," J Assist Reprod Genet. 37(2):347-357 (Feb. 2020).
Paulsen et al., "Translation of a human induced pluripotent stem cell-derived ovarian support cell product to a Phase 3 enabling clinical grade product for in vitro fertilization treatment," medRxiv. (Apr. 5, 2025) (44 pages).

(56) References Cited

OTHER PUBLICATIONS

Liu et al., "Transplantation of ovarian granulosa-like cells derived from human induced pluripotent stem cells for the treatment of murine premature ovarian failure," Molecular Medicine Reports. 13:5053-5058 (2016) (10 pages).
Piechota et al., "Human-induced pluripotent stem cell-derived ovarian support cell co-culture improves oocyte maturation in vitro after abbreviated gonadotropin stimulation," Hum Reprod. 38(12):2456-2469 (Dec. 2023).
Paulsen et al., "Development of human induced pluripotent stem cell-derived ovarian support cells as a clinical-grade product for in vitro fertilization," Cell Stem Cell. 33:1-15 (includes supplemental content) (Jan. 2026) (45 pages).
Bothun et al., "Steps toward the generation of ovarian somatic cells from pluripotent stem cells," Clinical Theriogenology. 12(4):529-535 (Dec. 2020).
Jahromi et al., "The potential role of granulosa cells in the maturation rate of immature human oocytes and embryo development: A co-culture study," Clin Exp Reprod Med. 42(3):111-7 (Sep. 2015).
Horvath, "DNA methylation age of human tissues and cell types," Genome Biology. 14:R115 (2013) (19 pages).
Frobel et al., "Epigenetic Rejuvenation of Mesenchymal Stromal Cells Derived from Induced Pluripotent Stem Cells," Stem Cell Reports. vol. 3:414-422 (2014) (9 pages).
Itami et al., "Age-associated changes in bovine oocytes and granulosa cell complexes collected from early antral follicles," J Assist Reprod Genet. 31:1079-1088 (2014) (10 pages).
Communication pursuant to Rule 114(2) EPC for European Patent Application No. 23741889.2, dated May 7, 2025 (3 pages).
Communication pursuant to Rule 114(2) EPC for European Patent Application No. 23741889.2, dated Jul. 2, 2025 (3 pages).
Communication pursuant to Rules 161(1) and 162 EPC for European Patent Application No. 23741889.2, dated Feb. 6, 2025 (3 pages).
Communication pursuant to Article 94(3) EPC for European Patent Application No. 23741889.2, dated Oct. 24, 2025 (8 pages).
Communication pursuant to Rule 114(2) EPC for European Patent Application No. 23741889.2, dated Mar. 9, 2026 (4 pages).
Response to Communication under Rules 161(1) and 162 EPC for European Patent Application No. 23741889.2, dated Aug. 6, 2025 (10 pages).
Response to Communication under Article 94(3) EPC for European Patent Application No. 23741889.2, dated Feb. 24, 2026 (10 pages).
Woods et al., "Revisiting Claims of the Continued Absence of Functional Germline Stem Cells in Adult Ovaries," Stem Cells. 41(2):200-204 (Dec. 2022) (6 pages).
Yoshihara et al., "In Reply: Revisiting Claims of the Continued Absence of Functional Germline Stem Cells in Adult Ovaries," Stem Cells. 41(2):205-206 (Mar. 2023).
Wagner et al., "Single-cell analysis of human ovarian cortex identifies distinct cell populations but no oogonial stem cells," Nat Commun. 11(1):1147 (Mar. 2020) (15 pages).
*Westmoreland County Employee Retirement System* v. *OvaScience, Inc., et al.*, Class Action Complaint for Violations of the Securities Act of 1933, United States District Court District of Massachusetts. Filed on Nov. 22, 2017 (53 Pages).
De Vos et al., "Clinical procedures for in vitro maturation treatment," Fertil Steril. 122(4):753-755. (Oct. 2024).
Chian et al., "IVM of human immature oocytes for infertility treatment and fertility preservation," Reprod Med Biol. 22(1):e12524 (Jul. 2023) (13 pages).

* cited by examiner

236

| Training Data 204 | |
|---|---|
| Measured Hormone Index | Pre-Culture Group COC Image |
| Patient Age | Post-Culture Group COC Image |
| Patient BMI | Post-Culture Denuded Oocyte Image |
| Number Of COCs Retrieved | Embryologist Notes |
| AMH Levels (ug/L) | Machine Learning Feedback |
| Antral Follicle Count (AFC) at Last Ultrasound | Follicular Dynamics Information |
| Patient Oocyte Retrieval Day E2 Levels (ng/L) | Study Sample Sheet |
| Patient Oocyte Retrieval Day P4 Levels (ng/L) | Frozen Oocyte Cell Lysate |
| Patient Oocyte Retrieval Day LH (IU/L) | Frozen Granulosa Cells Lysate |
| Patient Oocyte Retrieval Day FSH (IU/L) | Frozen Cell Culture Media |
| Stimulation Protocol | Oocyte Analytical Index |

*FIG. 2B*

400

| **Metabolite 404** | **Stock Solution Preparation Concentration 408** | **Final Concentration in IVM Media 412** |
|---|---|---|
| HSA | 100mg/ml | 10mg/ml |
| FSH | 75IU/ml | 75mIU/ml |
| hCG | 100IU/ml | 100mIU/ml |
| Androstenedione | 1mg/ml | 500ng/ml |
| Doxycycline | 2mg/ml | 1ug/ml |

*FIG. 4*

APPARATUS AND METHOD FOR INDUCING HUMAN OOCYTE MATURATION IN VITRO

FIELD OF THE INVENTION

The present invention generally relates to the field of in vitro maturation. In particular, the present invention is directed to an apparatus and method for inducing human oocyte maturation in vitro.

BACKGROUND

One in ten women struggle with infertility, requiring assisted reproductive technology such as in vitro fertilization (IVF). Challenges remain with maintaining oocyte health in culture, resulting in low oocyte quality and subsequently poor embryo quality. Furthermore, oocytes that are developmentally immature are traditionally discarded, constricting the available oocyte pool for IVF.

SUMMARY OF THE DISCLOSURE

In an aspect, an apparatus for aiding in human oocyte maturation in vitro, the apparatus including: a computing device, wherein the computing device includes at least a processor; and a memory communicatively connected to the at least processor, the memory containing instructions configuring the at least processor to receive first biological sample data from a first biological sample relating to a user; assign the user to a stimulation protocol as a function of the first biological sample; receive second biological sample data from a second biological sample relating to the user wherein the second biological sample comprises at least an immature oocyte; receive culture data relating the second biological sample; and assign the second biological sample a scoring metric as a function of the culture data of the second biological sample.

In another aspect, a method for inducing human oocyte maturation in vitro, the method including receiving a first biological sample relating to a user; assigning the user to a stimulation protocol as a function of the first biological sample; receiving a second biological sample relating to the user wherein the second biological sample includes at least an immature oocyte; culturing the second biological sample; and assigning the second biological sample a scoring metric as a function of culturing the second biological sample.

These and other aspects and features of non-limiting embodiments of the present invention will become apparent to those skilled in the art upon review of the following description of specific non-limiting embodiments of the invention in conjunction with the accompanying drawings.

BRIEF DESCRIPTION OF THE DRAWINGS

For the purpose of illustrating the invention, the drawings show aspects of one or more embodiments of the invention. However, it should be understood that the present invention is not limited to the precise arrangements and instrumentalities shown in the drawings, wherein:

FIG. 2B is an exemplary table illustrating training data for training a machine learning model;

FIG. 4 is an exemplary table of metabolite formulations;

The drawings are not necessarily to scale and may be illustrated by phantom lines, diagrammatic representations and fragmentary views. In certain instances, details that are not necessary for an understanding of the embodiments or that render other details difficult to perceive may have been omitted.

DETAILED DESCRIPTION

At a high level, aspects of the present disclosure are directed to apparatus and methods for inducing human oocyte maturation in vitro.

Aspects of the present disclosure can be used to increase the overall pool of available healthy oocytes in women for use in IVF. Aspects of the present disclosure can also be used to significantly reduce FSH dosing in patients during egg retrieval and improve oocyte quality in culture. This may greatly expand access to reproductive technology, make the duration of a single cycle significantly shorter and require less cycles overall to achieve pregnancy.

Exemplary embodiments illustrating aspects of the present disclosure are described below in the context of several specific examples.

Figure 1:
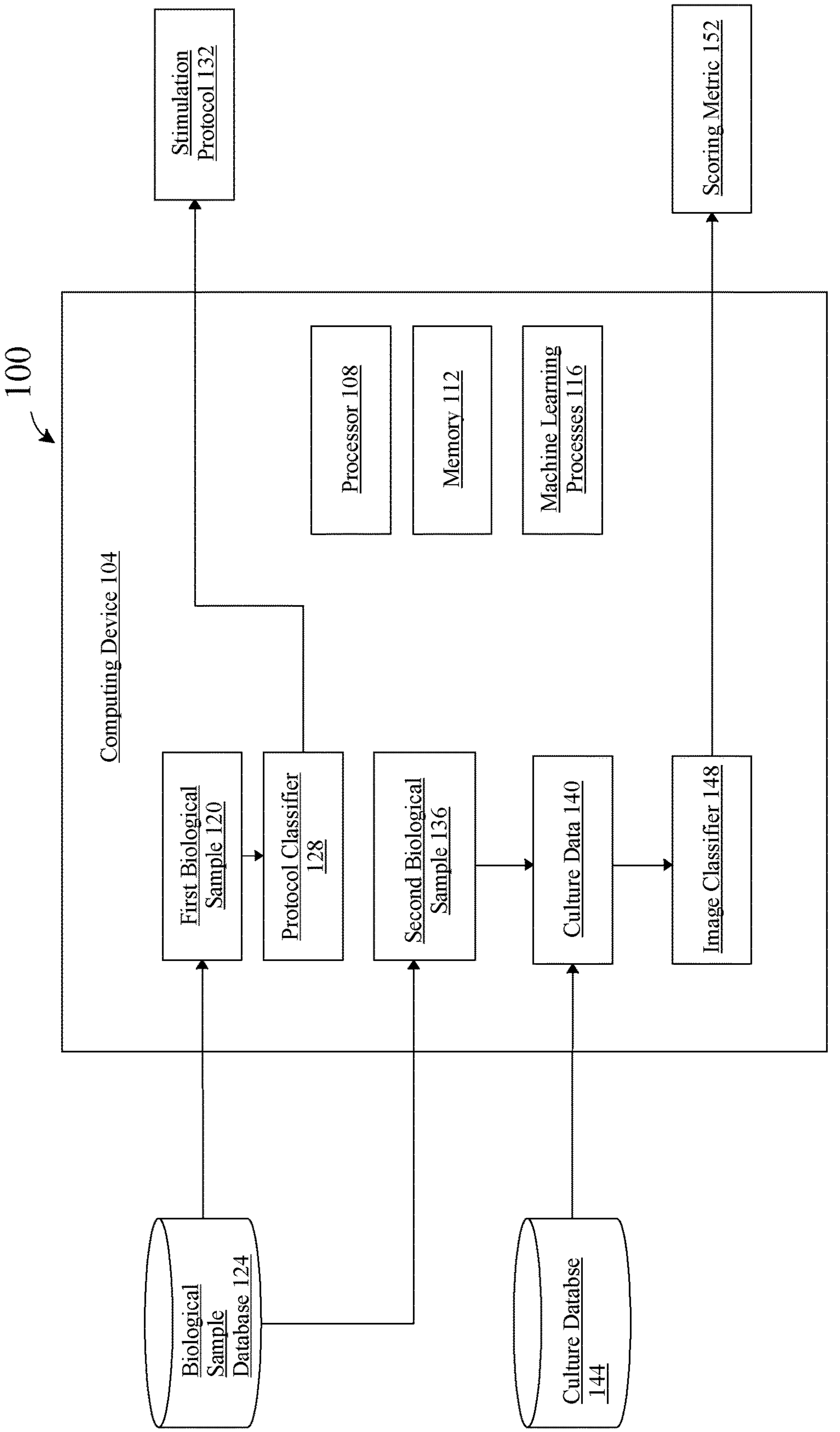
FIG. 1 is a block diagram of an embodiment of an apparatus for aiding in human oocyte maturation in vitro.

Referring now to FIG. 1, an exemplary embodiment of an apparatus 100 for inducing human oocyte maturation in vitro is illustrated. Apparatus 100 includes a computing device 104. Computing device 104 includes a processor 108 and a memory 112 communicatively connected to the processor 108, wherein memory 112 contains instructions configuring processor 108 to carry out the linking process. Processor 108 and memory 112 is contained in a computing device 104. Computing device 104 may include any computing device as described in this disclosure, including without limitation a microcontroller, microprocessor, digital signal processor (DSP) and/or system on a chip (SoC) as described in this disclosure. Computing device may include, be included in, and/or communicate with a mobile device such as a mobile telephone or smartphone. Computing device 104 may include a single computing device operating independently, or may include two or more computing device operating in concert, in parallel, sequentially or the like; two or more computing devices may be included together in a single computing device or in two or more computing devices. Computing device 104 may interface or communicate with one or more additional devices as described below in further detail via a network interface device. Network interface device may be utilized for connecting computing device 104 to one or more of a variety of networks, and one or more devices. Examples of a network interface device include, but are not limited to, a network interface card (e.g., a mobile network interface card, a LAN card), a modem, and any combination thereof. Examples of a network include, but are not limited to, a wide area network (e.g., the Internet, an enterprise network), a local area network (e.g., a network associated with an office, a building, a campus or other relatively small geographic space), a telephone network, a data network associated with a telephone/voice provider (e.g., a mobile communications provider data and/or voice network), a direct connection between two computing devices, and any combinations thereof. A network may employ a wired and/or a wireless mode of communication. In general, any network topology may be used. Information (e.g., data, software etc.) may be communicated to and/or from a computer and/or a computing device. Computing device 104 may include but is not limited to, for example, a computing device or cluster of computing devices in a first location and a second computing device or cluster of computing devices in a second location. Computing device 104 may include one or more computing devices dedicated to data storage, security, distribution of traffic for load balancing, and the like. Computing device 104 may distribute one or more computing tasks as described below across a plurality of computing devices of computing device, which may operate in parallel, in series, redundantly, or in any other manner used for distribution of tasks or memory between computing devices. Computing device 104 may be implemented using a "shared nothing" architecture in which data is cached at the worker, in an embodiment, this may enable scalability of system 100 and/or computing device.

With continued reference to FIG. 1, computing device 104 may be designed and/or configured to perform any method, method step, or sequence of method steps in any embodiment described in this disclosure, in any order and with any degree of repetition. For instance, computing device 104 may be configured to perform a single step or sequence repeatedly until a desired or commanded outcome is achieved; repetition of a step or a sequence of steps may be performed iteratively and/or recursively using outputs of previous repetitions as inputs to subsequent repetitions, aggregating inputs and/or outputs of repetitions to produce an aggregate result, reduction or decrement of one or more variables such as global variables, and/or division of a larger processing task into a set of iteratively addressed smaller processing tasks. Computing device 104 may perform any step or sequence of steps as described in this disclosure in parallel, such as simultaneously and/or substantially simultaneously performing a step two or more times using two or more parallel threads, processor cores, or the like; division of tasks between parallel threads and/or processes may be performed according to any protocol suitable for division of tasks between iterations. Persons skilled in the art, upon reviewing the entirety of this disclosure, will be aware of various ways in which steps, sequences of steps, processing tasks, and/or data may be subdivided, shared, or otherwise dealt with using iteration, recursion, and/or parallel processing.

With continued reference to FIG. 1, additionally, computing device 104 may perform determinations, classification, and/or analysis steps, methods, processes, or the like as described in this disclosure using machine learning processes 116. A "machine learning process," as used in this disclosure, is a process that automatedly uses a body of data known as "training data" and/or a "training set" (described further below) to generate an algorithm that will be performed by a computing device/module to produce outputs given data provided as inputs; this is in contrast to a non-machine learning software program where the commands to be executed are determined in advance by a user and written in a programming language. Machine-learning process 116 may utilize supervised, unsupervised, lazy-learning processes and/or neural networks, described further below.

With continued reference to FIG. 1, computing device 104 is configured to aid in human oocyte maturation in vitro by promoting rapid and efficient oocyte maturation in a manner that reinforces oocyte health and developmental competence. Computing device 104 is configured to receive first biological sample data from a first biological sample 120 relating to a user. As used in this disclosure, "biological sample data" is data that provides a characterization of the biological, genetic, biochemical and/or physiological properties, compositions, or activities of biological samples. A "biological sample" is any information relating to a user. A biological sample may include laboratory specimen held by a biorepository for research. In some embodiments, first biological sample 120 may include bodily fluids and/or data describing bodily fluids including blood, saliva, urine, semen (seminal fluid), vaginal secretions, cerebrospinal fluid (CSF), synovial fluid, pleural fluid (pleural lavage), pericardial fluid, peritoneal fluid, amniotic fluid, saliva, nasal fluid, optic fluid, gastric fluid, breast milk, cell culture supernatants, and the like. Biological sample data may include information describing a characterization of the biological, genetic, biochemical and/or physiological properties, compositions, or activities of biological samples. A biological sample may include a biological laboratory specimen held by a biorepository for research. A biological sample may include data describing one or more biological laboratory specimens. A biological sample may include data describing any information relating to a user. A biological sample may include a medical diagnosis, user input describing how a user is feeling and/or a symptomatic complaint, information collected from a wearable device pertaining to a user and the like. A biological sample may be collected from a user based on a survey, questionnaire, health history form, medical record, consultation, interview and the like collected from a user, third party such as a spouse or caregiver, and/or a medical professional such as a medical doctor, nurse, physician assistant, and the like. A "wearable device," as used in this disclosure, is any device worn close to and/or on the surface of the skin of a user. A wearable device may detect, analyze, and/or transmit information concerning one or more body signals of a user including but not limited to vital signs, ambient, data, biofeedback data and the like. A wearable device may include an activity tracker. A wearable device may receive and/or transmit data utilizing the internet of things (IOT). For example, a biological sample may include information obtained from a visit with a medical professional such as a health history. In yet another non-limiting example, a biological sample may include information such as data collected from a wearable device worn by a user and designed to collect information relating to a user's sleep patterns, exercise patterns, and the like. In some embodiments, an oocyte may be an immature oocyte. In an embodiment, first biological sample 120 may be collected at a particular date and/or time of a user's menstrual cycle. For instance and without limitation, first biological sample 120 may be collected on the second day of a user's menstrual cycle to evaluate one or more hormone levels such as E2, FSH, LH, P4, and/or AMH. First biological sample 120 may be utilized to determine one or more markers of a user's overall health including but not limited to ovarian reserve health and/or circulating hormone levels. This information may be utilized for example by a health care professional to monitor cycle progression and inform protocol and/or drug selection as described in more detail below. As used in this disclosure, a "user" is a living organism such as a human being, plant, animal, and all other organisms composed of cells. In some embodiments, the biological sample may be extracted from the user through an extraction device. An "extraction device" is a device and/or tool capable of obtaining, recording and/or ascertaining a measurement associated with a sample. The extraction device may include a needle, syringe, vial, lancet, Evacuated Collection Tubes (ECT), tourniquet, vacuum extraction tube systems, any combination thereof and the like. For example, the extraction device may comprise a butterfly needle set. Computing device 104 may receive the biological sample in the form of data uploaded to the memory. Data may include measurements, for example, of serum calcium, phosphate, electrolytes, blood urea nitrogen and creatinine, uric acid, and the like.

Still referring to FIG. 1, computing device 104 may receive first biological sample data from a biological sample database 124. A "biological sample database" is a database containing all data related biological samples of users containing analytic information. In some embodiments, biological sample database 124 may contain a systemic hormone index. A "systemic hormone index," as used in this disclosure, is data structure correlating medical knowledge regarding systemic hormone therapy. For example, systemic hormone index may include side effects and risks, proper methods of administering hormones, correlations between E2, LH, FSH, and/or P4 deficiency and systemic hormones and the like. In some embodiments, biological sample database 124 may be communicatively connected to computing device 104. As used in this disclosure, "communicatively connected" means connected by way of a connection, attachment, or linkage between two or more relata which allows for reception and/or transmittance of information therebetween. For example, and without limitation, this connection may be wired or wireless, direct, or indirect, and between two or more components, circuits, devices, systems, and the like, which allows for reception and/or transmittance of data and/or signal(s) therebetween. Data and/or signals therebetween may include, without limitation, electrical, electromagnetic, magnetic, video, audio, radio, and microwave data and/or signals, combinations thereof, and the like, among others. A communicative connection may be achieved, for example and without limitation, through wired or wireless electronic, digital, or analog, communication, either directly or by way of one or more intervening devices or components. Further, communicative connection may include electrically coupling or connecting at least an output of one device, component, or circuit to at least an input of another device, component, or circuit. For example, and without limitation, via a bus or other facility for intercommunication between elements of a computing device. Communicative connecting may also include indirect connections via, for example and without limitation, wireless connection, radio communication, low power wide area network, optical communication, magnetic, capacitive, or optical coupling, and the like. In some instances, the terminology "communicatively coupled" may be used in place of communicatively connected in this disclosure.

Still referring to FIG. 1, biological sample database 124, and all other databases described throughout this disclosure, may be implemented, without limitation, as a relational database, a key-value retrieval database such as a NOSQL database, or any other format or structure for use as a database that a person skilled in the art would recognize as suitable upon review of the entirety of this disclosure. Biological sample database 124 may alternatively or additionally be implemented using a distributed data storage protocol and/or data structure, such as a distributed hash table or the like. Biological sample database 124 may include a plurality of data entries and/or records as described above. Data entries in a database may be flagged with or linked to one or more additional elements of information, which may be reflected in data entry cells and/or in linked tables such as tables related by one or more indices in a relational database. Persons skilled in the art, upon reviewing the entirety of this disclosure, will be aware of various ways in which data entries in a database may store, retrieve, organize, and/or reflect data and/or records as used herein, as well as categories and/or populations of data consistently with this disclosure.

Still referring to FIG. 1, computing device 104 is configured to assign a user to a stimulation protocol 132 as a function of first biological sample 120. In some embodiments, the stimulation protocol 132 may be assigned based on a measured hormone level of the biological sample. A "stimulation protocol" is a medication injection process spanning over a specified period of time to induce ovaries in producing one or more oocytes. As used in this disclosure, a "measured hormone level" is a quantitative value representing a level of one or more hormones of a user. The measured hormone level of the biological sample may include estradiol (E2), luteinizing hormone (LH), follicle-stimulating hormone (FSH), progesterone (P4), estrone (E1), estriol (E3), testosterone, androgens, dehydroepiandrosterone (DHEA), triiodothyronine (T3), tetraiodothyronine (T4), calcitonin, melatonin, insulin, cortisol, human growth hormone (HGH), adrenaline levels and the like. In some embodiments, the measurement of hormone levels may be based on blood analysis a of the biological sample. For example, blood analysis may include plasma hormone analysis techniques. In some embodiments, measurement of hormone levels may be based on saliva hormone testing techniques. Measurement of hormone levels may be based on other forms of analysis such as hair, urine, and any other form of biological samples described throughout this disclosure. In an embodiment, selection of a stimulation protocol may be done utilizing information obtained from an ultrasound. An "ultrasound," as used in this disclosure, is any procedure that utilizes sound waves to generate one or more images of a user's body. For example, an ultrasound may be utilized to obtain an image of a woman's reproductive organs and/or tissues. In an embodiment, an ultrasound may be performed at a particular time of a woman's menstrual cycle. For example, a woman may receive an ultrasound on day 2 of her cycle and this may be utilized to determine follicle size and/or follicle count. Selection of a stimulation protocol and/or adjustment to a stimulation protocol may be made utilizing this information. For example, a woman with an ultrasound that shows polycystic ovarian syndrome (PCOS) may have a dose adjustment made to one or more medications received and/or utilized during a stimulation protocol. In addition, the length of her stimulation protocol may be modified based on her PCOS diagnosis. In an embodiment, an ultrasound may be repeated one or more times throughout a woman's stimulation protocol, and information obtained may be utilized to adjust her stimulation protocol in real time. In addition, a woman's contraception usage may affect assignment of a stimulation protocol. "Contraception," as used in this disclosure, is any method and/or device utilized to prevent pregnancy as a consequence of sexual intercourse. This may include but is not limited to any medication, technique, device, and/or birth control utilized by a woman. A woman's use of contraception or not may aid in determining at what point in the woman's menstrual cycle she should begin her stimulation protocol. For instance and without limitation, a woman who is not using any form of contraception may begin her stimulation protocol with recombinant follicle stimulating hormone (rFSH) on the second day of her menstrual cycle. In yet another non-limiting example, a woman who is using contraception may begin her stimulation protocol with rFSH 5 days after consuming her last oral contraception pill. In an embodiment, rFSH stimulation may be utilized for 2-3 days, depending on a patient's tolerance, follicle size, and/or growth dynamics. After this 2-3 day window, a coasting period of 1-2 days may be utilized to monitor follicle size and allow for further follicle maturation and development. A "coasting period," as used in this disclosure, is any period of time when a medication used throughout a stimulation protocol is not administered and/or consumed. A coasting period may last for example for 1 day, 2 days, 3 days, and the like. During a coasting period, a patient may continue to receive one or more ultrasounds to monitor her progression. Once a follicle size has reached anywhere from between 8-10 mm, a patient may be triggered with a dose of human chorionic gonadotropin (hcG). In an embodiment, a double hcG injection may be utilized, to induce follicle maturation to prepare one or more follicles for retrieval. A blood test for one or more hormone levels such as E2, P4, and LH may be performed on trigger day of double dose of human chorionic gonadotropin (hcG) injection to monitor hormone levels. After the day of the double dose of hcG, one or more hormone levels may be measured such as for example a blood test to determine and examine doses of E2, P4, and LH. Approximately 24-48 hours after the dose of hcG that is administered, a patient may undergo an oocyte retrieval. On the day of oocyte retrieval, a blood test for one or more hormone levels such as E2, LH, and/or P4 may be performed to ensure quality metrics, hormone levels are within range, and/or that hcG dose was ingested. The assigned stimulation protocol 132 may include a minimal stimulation protocol configured to trigger the release of a cell in the span of 3 days. A "minimal stimulation protocol" is a stimulation process spanning over a shortened period of time, compared to average in vitro fertilization (IVF) stimulation protocols, to aid in inducing an ovary to produce an egg. Typically, the average span of time for a stimulation protocol using standard IVF is around 8-14 days. The minimal stimulation protocol may induce the release of a cell in of 2-6 days, which is a shorted period of time compared to 8-14 days. The average time for performing minimal stimulation protocol 132 may be 3 days. The max time may be 6 days and the minimal amount of time may be 2 days. In an embodiment, the minimal stimulation protocol may include selecting a first triggering agent as a function of the first biological sample 120 and selecting a second triggering agent as a function of a follicle measurement, which is disclosed in greater detail below. A "follicle measurement" as used in this disclosure, is any measurement of an ovarian follicle. A follicle may include any sac found in an ovary that contains an unfertilized egg. A follicle measurement may be obtained using any methodology as described herein, including for example an ultrasound, a manual measurement, an automated measurement and the like. A "triggering agent" is a chemical that triggers cell generation in the ovaries. A triggering agent may include any substance including any non-prescription and/or prescription product. A triggering agent may include for example, Lupron as produced by Abbott Laboratories, headquartered in North Chicago, IL; Ganirelix as produced by Ferring Pharmaceuticals, headquartered in Saint-Prex, Switzerland; Cetrotide as produced by Merck Global, headquartered in Whitehouse Station, Readington Township, NJ; Gonal-F as produced by Merck Global, Follistim as produced by Merck Global; Bravelle as produced by Ferring Pharmaceuticals, headquartered in Saint-Prex; Switzerland, Clomid as produced by Patheon Pharmaceuticals Inc., headquartered in Waltham, MA; Serephene as produced by Teva, headquartered in Tel Aviv-Yafo, Israel; Glucophage as produced by Merck Global; Fortamet as produced by Mylan, headquartered in Canonsburg, PA; Pregnyl as produced by Schering Plough, headquartered in Kenilworth, NJ; Novarel as produced by Ferring Laboratories, headquartered in Parsippany, NJ; Repronex as produced by Ferring Pharmaceuticals, Inc.; Factrel as produced by Zoetis Canada Inc., headquartered in Kirkland, Canada, Menopur as produced by Ferring Pharmaceuticals, and other drugs that induce cell generation in ovaries that one skilled in the art would understand as applicable. A triggering agent may include human serumalbumin, FSH, hCG, androstenedione, and doxycycline as described in formulations disclosed further below. Computing device 104 may assign the triggering agents used based on the measured hormone levels of first biological sample 120. In some embodiments, computing device 104 may use a machine learning process to generate and/or train a machine-learning model including a classifier.

In an embodiment, and continuing to refer to FIG. 1, a machine-learning model may be utilized to assign a user to a particular stimulation protocol as a function of first biological sample 120. A "classifier," as used in this disclosure is a machine-learning model, such as a mathematical model, neural net, or program generated by a machine learning algorithm known as a "classification algorithm," as described in further detail below, that sorts inputs into categories or bins of data, outputting the categories or bins of data and/or labels associated therewith. A classifier may be configured to output at least a datum that labels or otherwise identifies a set of data that are clustered together, found to be close under a distance metric as described below, or the like. Computing device 104 and/or another device may generate protocol classifier 128 using a classification algorithm. A "protocol classifier" is a classifier trained to intake biological samples relating to a user and output/assign stimulation protocol 132 to the related user based on training data received. Training data may consist of inputs and/or outs containing systemic hormone index data, feedback from past stimulation protocol 132 assignments, and any other data described throughout this disclosure. Training data may be received from biological sample database 124. In some embodiments, training data may include a plurality of data entries containing biological samples correlated to outputs containing assigned stimulation protocols. In some embodiments, training data may include inputs such as assigned stimulation protocols correlated to outputs such as pregnancy success rate or scoring metrics as described throughout this disclosure. In some embodiments, training data may include correlations between a stimulation protocol and the correlated side effects. In some embodiments, training data may include methods and procedures to prevent hyperstimulation of the ovaries by the triggering agent. For example, training data may include the number of injections a user may receive containing a specific triggering agent at a plurality of doses before hyperstimulation occurs.

Still referring to FIG. 1, classification may be performed using, without limitation, linear classifiers such as without limitation logistic regression and/or naive Bayes classifiers, nearest neighbor classifiers such as k-nearest neighbors classifiers, support vector machines, least squares support vector machines, fisher's linear discriminant, quadratic classifiers, decision trees, boosted trees, random forest classifiers, learning vector quantization, and/or neural network-based classifiers. Computing device 104 may be configured to generate a classifier using a Naïve Bayes classification algorithm. Naïve Bayes classification algorithm generates classifiers by assigning class labels to problem instances, represented as vectors of element values. Class labels are drawn from a finite set. Naïve Bayes classification algorithm may include generating a family of algorithms that assume that the value of a particular element is independent of the value of any other element, given a class variable. Naïve Bayes classification algorithm may be based on Bayes Theorem expressed as P(A/B)=P(B/A) P(A)=P(B), where P(A/B) is the probability of hypothesis A given data B also known as posterior probability; P(B/A) is the probability of data B given that the hypothesis A was true; P(A) is the probability of hypothesis A being true regardless of data also known as prior probability of A; and P(B) is the probability of the data regardless of the hypothesis. A naïve Bayes algorithm may be generated by first transforming training data into a frequency table. Computing device 104 may then calculate a likelihood table by calculating probabilities of different data entries and classification labels. Computing device 104 may utilize a naïve Bayes equation to calculate a posterior probability for each class. A class containing the highest posterior probability is the outcome of prediction. Naïve Bayes classification algorithm may include a gaussian model that follows a normal distribution. Naïve Bayes classification algorithm may include a multinomial model that is used for discrete counts. Naïve Bayes classification algorithm may include a Bernoulli model that may be utilized when vectors are binary.

With continued reference to FIG. 1, computing device 104 may be configured to generate a classifier using a K-nearest neighbors (KNN) algorithm. A "K-nearest neighbors algorithm" as used in this disclosure, includes a classification method that utilizes feature similarity to analyze how closely out-of-sample-features resemble training data to classify input data to one or more clusters and/or categories of features as represented in training data; this may be performed by representing both training data and input data in vector forms, and using one or more measures of vector similarity to identify classifications within training data, and to determine a classification of input data. K-nearest neighbors algorithm may include specifying a K-value, or a number directing the classifier to select the k most similar entries training data to a given sample, determining the most common classifier of the entries in the database, and classifying the known sample; this may be performed recursively and/or iteratively to generate a classifier that may be used to classify input data as further samples. For instance, an initial set of samples may be performed to cover an initial heuristic and/or "first guess" at an output and/or relationship, which may be seeded, without limitation, using expert input received according to any process as described herein. As a non-limiting example, an initial heuristic may include a ranking of associations between inputs and elements of training data. Heuristic may include selecting some number of highest-ranking associations and/or training data elements.

With continued reference to FIG. 1, generating k-nearest neighbors algorithm may generate a first vector output containing a data entry cluster, generating a second vector output containing an input data, and calculate the distance between the first vector output and the second vector output using any suitable norm such as cosine similarity, Euclidean distance measurement, or the like. Each vector output may be represented, without limitation, as an n-tuple of values, where n is at least two values. Each value of n-tuple of values may represent a measurement or other quantitative value associated with a given category of data, or attribute, examples of which are provided in further detail below; a vector may be represented, without limitation, in n-dimensional space using an axis per category of value represented in n-tuple of values, such that a vector has a geometric direction characterizing the relative quantities of attributes in the n-tuple as compared to each other. Two vectors may be considered equivalent where their directions, and/or the relative quantities of values within each vector as compared to each other, are the same; thus, as a non-limiting example, a vector represented as [5, 10, 15] may be treated as equivalent, for purposes of this disclosure, as a vector represented as [1, 2, 3]. Vectors may be more similar where their directions are more similar, and more different where their directions are more divergent; however, vector similarity may alternatively or additionally be determined using averages of similarities between like attributes, or any other measure of similarity suitable for any n-tuple of values, or aggregation of numerical similarity measures for the purposes of loss functions as described in further detail below. Any vectors as described herein may be scaled, such that each vector represents each attribute along an equivalent scale of values. Each vector may be "normalized," or divided by a "length" attribute, such as a length attribute I as derived using a Pythagorean norm $$l = \sqrt{\sum_{i=0}^{n} a_i^2},$$

where ai is attribute number i of the vector. Scaling and/or normalization may function to make vector comparison independent of absolute quantities of attributes, while preserving any dependency on similarity of attributes; this may, for instance, be advantageous where cases represented in training data are represented by different quantities of samples, which may result in proportionally equivalent vectors with divergent values.

Still referring to FIG. 1, computing device 104 is configured to receive second biological sample data from second biological sample 136 relating to the user, wherein second biological sample 136 includes at least an oocyte. An "oocyte," as used in this disclosure, is a reproductive cell originating in an ovary. An oocyte may include but is not limited to an immature oocyte, a mature oocyte, a group of one or more oocytes, a group of one or more cells, a cumulus oocyte complex and the like. A "cumulus oocyte complex," as used in this disclosure, is an oocyte containing one or more surrounding cumulus cells. A COC may contain an immature oocyte. A COC may contain a mature oocyte. An "immature oocyte" as used in this disclosure is one or more immature reproductive cells originating in the ovaries. In some embodiments, an immature oocyte may be an oocyte including but not limited to germinal vesicle (GV) and Metaphase 1 (M1) oocytes, as described further below. In some embodiments, an immature oocyte may be a plurality of oocytes. An immature oocyte may be immature cumulus-oocyte-complexes (COCs) taken from a patient. A "mature oocyte" as used in this disclosure, is one or more mature reproductive cells originating in the ovaries. Once retrieved, a COC may rest for 2-3 hours to allow for equilibration to in vitro conditions. granulosa cell. In an embodiment, an oocyte may be combined with a granulosa cell. A "granulosa cell" is a cumulus cell surrounding the oocyte to ensure healthy oocyte and embryo development. In an embodiment, a granulosa cell may be sourced from a human donor. In an embodiment, a granulosa cell may be sourced from a stem cell such as a pluripotent stem cell. In an embodiment, a granulosa cell may be sourced from an embryonic tissue, a fetal tissue, an adult tissue, and/or a differentiated somatic cell. In an embodiment, a granulosa cell may be grown and sourced by artificial means such as in a laboratory. In some embodiments, the immature oocyte may contain an oocyte wherein the granulosa cell is added to mature the oocyte in a cell culture and thus create a COC after extraction of second biological sample 136. Second biological sample 136 may include bodily fluids as disclosed above. In an embodiment, one or more granulosa cells may be thawed during resting period of one or more COCs. In an embodiment, anywhere from between 50,000-100,000 granulosa cells may be combined with a COC during culturing. In an embodiment, thawed granulosa cells may be placed into a culture medium prior to COC retrieval, including anywhere form 24-120 hours beforehand. A COC may be transferred into culture medium containing thawed granulosa cells to form a group culture as described below in more detail. In an embodiment, a group culture may be culture in an incubator from ranging in time from anywhere from 12-48 hours. Computing device 104 may receive second biological sample data form biological sample database 124 as described above. Second biological sample 136 may be extracted using an extraction device and received as disclosed above. In some embodiments, computing device 104 may record the measured hormone level of second biological sample 136 using methods as disclosed above. Granulosa cells may be produced using Clustered Regularly Interspaced Short Palindromic Repeats (CRISPR) technology. "CRISPR" is programmable technology that targets specific stretches of genetic code to edit DNA at precise locations. CRISPR technology may include CRISPR-CAS 9. Cas9 (or "CRISPR-associated protein 9") is an enzyme that uses CRISPR sequences as a guide to recognize and cleave specific strands of DNA that are complementary to the CRISPR sequence. Cas9 enzymes together with CRISPR sequences form the basis of a technology known as CRISPR-Cas9 that can be used to edit genes within organisms. CRISPR technology may include Class 1 CRISPR systems including type I (cas3), type III (cas10), and type IV and 12 subtypes. CRISPR technology may include Class 2 CRISPR systems including type II (cas9), type V (cas12), type VI (cas13), and 9 subtypes. In some embodiments, CRISPR technology may involve CRISPR-Cas design tools which are computer software platforms and bioinformatics tools used to facilitate the design of guide RNAs (gRNAs) for use with the CRISPR/Cas gene editing system. For example, CRISPR-Cas design tools may include: CRISPRon, CRISPRoff, Invitrogen TrueDesign Genome Editor, Breaking-Cas, Cas-OFFinder, CASTING, CRISPy, CCTop, CHOPCHOP, CRISPOR, sgRNA Designer, Synthego Design Tool, and the like. CRISPR technology may also be used as a diagnostic tool. For example, CRISPR-based diagnostics may be coupled to enzymatic processes, such as SHERLOCK-based Profiling of IN vitro Transcription (SPRINT). SPRINT can be used to detect a variety of substances, such as metabolites in patient samples or contaminants in environmental samples, with high throughput or with portable point-of-care devices.

Still referring to FIG. 1, computing device 104 is configured to receive culture data 140 relating to second biological sample 136. "Culture data" is data that provides a characterization of the biological, genetic, biochemical and/or physiological properties, compositions, or activities of cell cultured biological samples. Culture data 140 may include recording data and identifying growth trends of the COCs formed as a result of adding the granulosa cells to the second biological extraction. In an embodiment, second biological sample 136 may rest in culture media for 2-3 hours after retrieval to allow for equilibration to in vitro conditions. Computing device 104 may receive culture data 140 from a culture sample database 144. A "culture sample database" is a database including analytical data regarding the culturing process and methods of second biological sample 136. For example, culture data 140 may be images of the cultured second biological sample 136, wherein computing device 104 may be configured to analyze the images for results, objectives, and the like. In some embodiments, computing device 104 may receive data such as embryologist notes regarding the process, results, objectives, and the like of cultured second biological sample 136 from culture sample database 144. Culture sample database 144 may be communicatively connected to computing device 104 and implemented as described above. In some embodiments, culture sample database 144 may include an oocyte analytical index. A "oocyte analytical index" is a data structure containing, rubrics, analytical methods, and approaches to analyzing cell culture media. For example, the oocyte analytical index may include methods to oocyte scoring, outcome analysis, cofounding variable analysis, and the like.

In some embodiments regarding the culture of second biological sample 136, cell culture media may include LAG media. For example, LAG media may be used for the incubation of COCs post-retrieval from stimulation protocol 132. Package size may be a 10 ml vial. Storage may be at 2-8° C. away from light up to one month. Media equilibration may be 18 to 24 hours pre-culture, include a seed 100 ul droplet and placed into 37C incubator with 6% O2 and proper CO2. In some embodiments, cell culture media may include IVM media. For example, a modified-MediCult IVM media may be used a baseline control during the culturing process. Package size may be a 10 ml vial. Storage may be at 2-8° C. away from light up to one month. In some embodiments, the cell culture mediums may include metabolites. For example, the modified-MediCult IVM media may include human serum albumin, FSH, hCG, Androstenedione, Doxycycline and other compounds. Other cell culture material and equipment may include: liquid nitrogen, hyaluronidase, dPBS, IVF-Qualified mineral oil, universal GPS dishes, G-NOPS plus media, micropipettes, stripper pipettors, camera-equipped inverted ICSI Microscope, Dry Inject Tabletop incubators, saturated humidity incubators, EmbryoScope, microcentrifuge, refrigerator, −20° ° C. freezer to 100° C. freezer, liquid nitrogen storage dewer, 35 mm dishes for denuding, stripper pipette tips, and other components one skilled in the art would understand to be included in the cell culture process.

Still referring to FIG. 1, in some embodiments, culturing second biological sample 136 may include culturing the immature Cumulus-Oocyte complexes in a group culture. A "group culture" is an extracted COC combined with one or more additional cells. An additional cell may include any cell grown together with an extracted COC. An additional cell may include a granulosa cell. In an embodiment, a group culture may be cultured and/or incubated for a particular length of time, such as from between 12-120 hours. For example, group culturing may include culturing the Cumulus-Oocyte complexes with a granulosa co-culture as described further below. A "co-culture" is a cell cultivation set-up, in which two or more different populations of cells are grown with some degree of contact between them. In some embodiments, group culturing may include culturing a control group of COCs with no co-culture, as described further below. In some embodiments, a user may donate immature oocytes, such as germinal vesicle (GV) and Metaphase 1 (M1) oocytes that may be used in medium as part of the group culture to help grow COCs. Oocyte donation may follow an oocyte retrieval process as discussed above. A user participating in oocyte donation may be different, or the same, from the user related to the second biological sample containing immature COCs. In some embodiments, oocyte donation user may undergo a stimulation protocol as disclosed above. In some embodiments, granulosa cells, cumulus cells, oocytes, GV oocytes, MI, oocytes, and all other types of cells described through this disclosure may be lysed, extracted for genomic material and flash frozen. For example, cells may undergo enzymatic cell lysis using enzymes such as lysozyme, lysostaphin, zymolase, cellulose, protease or glycanase, and the like. Other lysis methods may be applied such as, chemical lysis, detergent lysis, alkaline lysis, mechanical lysis, thermal lysis, acoustic lysis, physical lysis, non-mechanical lysis and the like. In some embodiments, culture media may be flash frozen. Freezing methods may include using a cryoprotective agent such as dimethyl sulfoxide and/or any other freezing method described through this disclosure.

Still referring to FIG. 1, computing device 104 is configured to assign second biological sample 136 a scoring metric 152 as a function of culturing second biological sample 136. A "scoring metric," as used in this disclosure, is a measure of quantitative assessment used for comparing, and tracking performance or production of oocyte maturation. In an embodiment, a scoring metric may be calculated after denuding. "Denuding," as used in this disclosure, is any process in which a cell may be removed from an oocyte. Denuding may include any mechanical and/or enzymatic process. For instance and without limitation denuding may include removing granulosa cells and/or cumulus cells from an oocyte. This may be performed mechanically and/or with one or more chemicals such as an enzyme to aid in the separation. Computing device 104 may receive patient information regarding the completion of the stimulation protocol 132 such as: patient Age, patient BMI, number of COCs retrieved, AMH Levels (ug/L), antral follicle count (AFC) at last ultrasound, patient oocyte retrieval day E2 Levels (ng/L), patient oocyte retrieval day P4 Levels (ng/L), patient oocyte retrieval day LH (IU/L), patient oocyte retrieval day FSH (IU/L), Days of stimulation, Gonadotropin used, and total injected dose (IU). Assigning the scoring metric 152 may include the computing device 104 analyzing imaged group culture of one or both of co-culture and no-co-culture growth groups. Computing device 104 may receive a: pre-culture group COC image, post-culture group COC image, and a post-culture denuded oocyte image. In some embodiments, images may be of frozen lysates and cell culture media. In an embodiment, scoring metric may include assessing a developmentally mature oocyte via microscopy for presence of a polar body. If a polar body is found, then the oocyte may be selected and utilized for intracytoplasmic sperm injection (ICSI) fertilization and/or oocyte freezing.

With continued reference to FIG. 1, in some embodiments, images may be sent to a third party for scoring assignment. A third party" is a qualified person or organization, such as an embryologist, to analyze the group cultures and develop/assign the scoring metric 152. Additionally, computing device 104 may perform any determinations, classification, and/or analysis steps, methods, processes, performed by a third party. In some embodiments the scoring metric 152 may include total oocyte scoring (TOS) as a function of analyzing the imaged group cultures. Oocyte scoring may include metrics such as shape, size, ooplasm characteristics, structure of the perivitelline space (PVS), zona pellucida (ZP), polar body (PB) morphology, and the like. "Oocyte scoring," as used in this disclosure, is a grading system assessing the production and quality of matured human oocytes. For example, computing device 104 may be configured to perform the total oocyte scoring on both pre and post culture oocyte images for generation of the TOS metric on a scale system of −6 to +6. Computing device 104 may generate and/or train a machine-learning model including a classification algorithm (image classifier 148) to perform the total oocyte scoring. The training data may include any data described throughout this disclosure, such as patient information, follicular dynamics information, oocyte scoring metric 152, study sample sheet (such as oocyte scoring metric 152 instruction set). Image classifier 148 may take the group culture images as an input, and by utilizing the training data, output the total oocyte score. Training data may include from culture sample database 144 as described above.

With continued reference to FIG. 1, a detailed disclosure of the machine learning model is described in further detail below. Regarding oocyte shape, if oocyte morphology is poor (dark general oocyte coloration and/or ovoid shape), it may be assigned a value of −1; if almost normal (less dark general oocyte coloration and less ovoid shape), it may be assigned a value of 0; if it is judged to be normal, it may be assigned a value of +1. Regarding oocyte size: if oocyte size is defined as abnormally small or large, it may be assigned a value −1 if size is below 120μ or greater 160μ. If the size is almost normal, i.e., did not deviate from normal by more than 10μ, a value of 0 may be assigned, and a value of +1 may be assigned if oocyte size is within normal range >130μ and <150μ. Regarding ooplasm characteristics, if the ooplasm is very granular and/or very vacuolated and/or demonstrated several inclusions, a value of −1 may assigned. If it is only slightly granular and/or demonstrated only few inclusions, a value of 0 may be assigned. Absence of granularity and inclusions may result in a +1 value. Regarding structure of the perivitelline space (PVS), the PVS may defined as −1 with an abnormally large PVS, an absent PVS or a very granular PVS. It may be assigned a value of 0 with a moderately enlarged PVS and/or small PVS and/or a less granular PVS. A value of +1 may be assigned to a normal size PVS with no granules. Regarding, zona pellucida (ZP), if ZPs is very thin or thick (<10μ or >20μ) the oocyte may be assigned a −1. If the ZP does not deviate from normal by more than 2μ it may be assigned 0. A normal zona (>12μ and <18μ) may be assigned a +1. Regarding polar body (PB) morphology, PB morphology is defined as follows: Flat and/or multiple PBs or zero PBs, granular and/or either abnormally small or large PBs is designated as −1. PBs, judged a fair but not excellent may be designated as 0, and a designation of +1 may be given to PBs of normal size and shape. In some embodiments, MII oocytes PB score may not be aggregated into TOS. In some embodiments, the TOS calculated by computing device 104 may be crossed checked against an embryologist or a similar person skilled in the art to solidify that the quality scoring was biased by image quality. Feedback relating to correction by a professional, adjustments, correlations may be added to the training data of the machine-learning model.

Still referring to FIG. 1, scoring metric 152 may include performing an outcome analysis as a function of the TOS. An "outcome analysis," as used in the disclosure, is a measurement of the maturation rate and oocyte quality scores between cultures in the group culture. Parametric or non-parametric tests may be applied to determine the significance of findings during the analysis. Computing device 104 may use a classification algorithm using methods described above to determine GV to MII oocyte maturation rate; GV to MI oocyte maturation rate; MI to MII oocyte maturation rate; Average Total Oocyte Score; Average Oocyte Shape; Average Oocyte Size; Average Ooplasm quality; Average PVS quality; Average ZP quality; Average Polar Body quality, and the like. In some embodiments these outcomes may reported as a as mean, median, and deviation.

In some embodiments, and with continued reference to FIG. 1, computing device 104 may conduct the outcome analysis using machine learning processes 116 and/or models as described throughout this disclosure. For example, computing device 104 may train a machine-learning model to output an outcome analysis based on inputted group culture images, wherein the training data includes oocyte scoring metrics, study sample sheet, patient information, feedback from computing device 104 programmers/third parties, data from assigned stimulation protocol, and all other forms of data described through this disclosure. Training data may come from biological sample database 124 and culture database 144. In some embodiments, communications from a third party may be inputted into a machine learning process 116 to create a machine-learning model to generate the scoring metric. For example, a third-party communication may contain embryologist notes related to total oocyte scoring, wherein the notes are inputted into a machine-learning model containing a classifier to generate the outcome analysis using training data, received biological sample database 124 and culture database 144, containing patient information, data from image classifier 148, data from assigned stimulation protocol, study sample sheet, and any other form of data described throughout this disclosure. Additionally or alternatively, communications relating to scoring metrics generated by the computing device may be sent to a third party may, using machine learning processes 116. For example, oocyte scoring metrics may be sent a third party operated remote computing device communicatively connected to computing device 104, wherein the third party may conduct further analysis such as the outcome analysis. Furthering this example, a third-party response to communications generated by computing device 104 may be uploaded into a database communicatively connected to computing device 104 and be used as feedback in training data.

Still referring to FIG. 1, in some embodiments, scoring metric 152 may include an Omics-based analysis. For example, frozen cell lysates and cell culture mediums may be analyzed for bulk RNA-sequencing, whole genome bisulfite sequencing (WGBS), mass spectrometry-based proteomics and metabolomics. Cell culture media may be utilized for metabolomics analysis to determine changes in molecular content of media following co-culture compared to pre-culture media controls. This may be utilized by computing device 104 to profile dynamic changes in paracrine signaling between granulosa cells and oocytes. The data gathered may then be aggregated for downstream analysis for determination of changes in epigenetic state, metabolite presence, and gene expression between different co-culture conditions and controls.

Figure 2A:
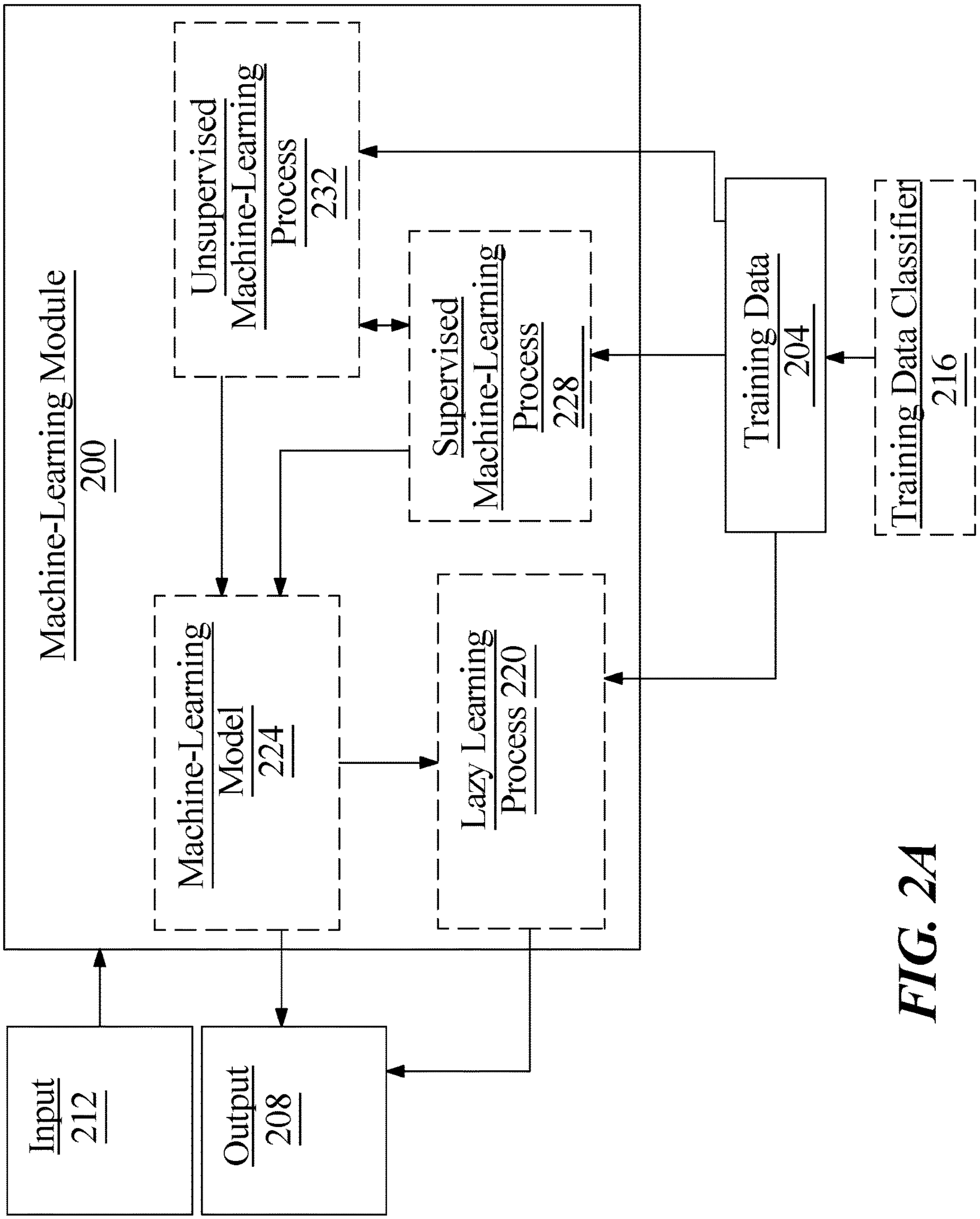
FIG. 2A is a block diagram of exemplary embodiment of a machine learning module.

Referring now to FIG. 2A, an exemplary embodiment of a machine-learning module 200 that may perform one or more machine-learning processes as described in this disclosure is illustrated. Machine-learning module may perform determinations, classification, and/or analysis steps, methods, processes, or the like as described in this disclosure using machine learning processes. A "machine learning process," as used in this disclosure, is a process that automatedly uses training data 204 to generate an algorithm that will be performed by a computing device/module to produce outputs 208 given data provided as inputs 212; this is in contrast to a non-machine learning software program where the commands to be executed are determined in advance by a user and written in a programming language.

Still referring to FIG. 2A, "training data," as used herein, is data containing correlations that a machine-learning process may use to model relationships between two or more categories of data elements. For instance, and without limitation, training data 204 may include a plurality of data entries, each entry representing a set of data elements that were recorded, received, and/or generated together; data elements may be correlated by shared existence in a given data entry, by proximity in a given data entry, or the like. Multiple data entries in training data 204 may evince one or more trends in correlations between categories of data elements; for instance, and without limitation, a higher value of a first data element belonging to a first category of data element may tend to correlate to a higher value of a second data element belonging to a second category of data element, indicating a possible proportional or other mathematical relationship linking values belonging to the two categories. Multiple categories of data elements may be related in training data 204 according to various correlations; correlations may indicate causative and/or predictive links between categories of data elements, which may be modeled as relationships such as mathematical relationships by machine-learning processes as described in further detail below. Training data 204 may be formatted and/or organized by categories of data elements, for instance by associating data elements with one or more descriptors corresponding to categories of data elements. As a non-limiting example, training data 204 may include data entered in standardized forms by persons or processes, such that entry of a given data element in a given field in a form may be mapped to one or more descriptors of categories. Elements in training data 204 may be linked to descriptors of categories by tags, tokens, or other data elements; for instance, and without limitation, training data 204 may be provided in fixed-length formats, formats linking positions of data to categories such as comma-separated value (CSV) formats and/or self-describing formats such as extensible markup language (XML), JavaScript Object Notation (JSON), or the like, enabling processes or devices to detect categories of data.

Alternatively or additionally, and continuing to refer to FIG. 2A, training data 204 may include one or more elements that are not categorized; that is, training data 204 may not be formatted or contain descriptors for some elements of data. Machine-learning algorithms and/or other processes may sort training data 204 according to one or more categorizations using, for instance, natural language processing algorithms, tokenization, detection of correlated values in raw data and the like; categories may be generated using correlation and/or other processing algorithms. As a non-limiting example, in a corpus of text, phrases making up a number "n" of compound words, such as nouns modified by other nouns, may be identified according to a statistically significant prevalence of n-grams containing such words in a particular order; such an n-gram may be categorized as an element of language such as a "word" to be tracked similarly to single words, generating a new category as a result of statistical analysis. Similarly, in a data entry including some textual data, a person's name may be identified by reference to a list, dictionary, or other compendium of terms, permitting ad-hoc categorization by machine-learning algorithms, and/or automated association of data in the data entry with descriptors or into a given format. The ability to categorize data entries automatedly may enable the same training data 204 to be made applicable for two or more distinct machine-learning algorithms as described in further detail below. Training data 204 used by machine-learning module 200 may correlate any input data as described in this disclosure to any output data as described in this disclosure.

Further referring to FIG. 2A, training data may be filtered, sorted, and/or selected using one or more supervised and/or unsupervised machine-learning processes and/or models as described in further detail below; such models may include without limitation a training data classifier 216. Training data classifier 216 may include a "classifier," which as used in this disclosure is a machine-learning model as defined below, such as a mathematical model, neural net, or program generated by a machine learning algorithm known as a "classification algorithm," as described in further detail below, that sorts inputs into categories or bins of data, outputting the categories or bins of data and/or labels associated therewith. A classifier may be configured to output at least a datum that labels or otherwise identifies a set of data that are clustered together, found to be close under a distance metric as described below, or the like. Machine-learning module 200 may generate a classifier using a classification algorithm, defined as a process whereby a computing device and/or any module and/or component operating thereon derives a classifier from training data 204. Classification may be performed using, without limitation, linear classifiers such as without limitation logistic regression and/or naive Bayes classifiers, nearest neighbor classifiers such as k-nearest neighbors classifiers, support vector machines, least squares support vector machines, fisher's linear discriminant, quadratic classifiers, decision trees, boosted trees, random forest classifiers, learning vector quantization, and/or neural network-based classifiers.

Still referring to FIG. 2A, machine-learning module 200 may be configured to perform a lazy-learning process 220 and/or protocol, which may alternatively be referred to as a "lazy loading" or "call-when-needed" process and/or protocol, may be a process whereby machine learning is conducted upon receipt of an input to be converted to an output, by combining the input and training set to derive the algorithm to be used to produce the output on demand. For instance, an initial set of simulations may be performed to cover an initial heuristic and/or "first guess" at an output and/or relationship. As a non-limiting example, an initial heuristic may include a ranking of associations between inputs and elements of training data 204. Heuristic may include selecting some number of highest-ranking associations and/or training data 204 elements. Lazy learning may implement any suitable lazy learning algorithm, including without limitation a K-nearest neighbors algorithm, a lazy naïve Bayes algorithm, or the like; persons skilled in the art, upon reviewing the entirety of this disclosure, will be aware of various lazy-learning algorithms that may be applied to generate outputs as described in this disclosure, including without limitation lazy learning applications of machine-learning algorithms as described in further detail below.

Alternatively or additionally, and with continued reference to FIG. 2A, machine-learning processes as described in this disclosure may be used to generate machine-learning models 224. A "machine-learning model," as used in this disclosure, is a mathematical and/or algorithmic representation of a relationship between inputs and outputs, as generated using any machine-learning process including without limitation any process as described above and stored in memory; an input is submitted to a machine-learning model 224 once created, which generates an output based on the relationship that was derived. For instance, and without limitation, a linear regression model, generated using a linear regression algorithm, may compute a linear combination of input data using coefficients derived during machine-learning processes to calculate an output datum. As a further non-limiting example, a machine-learning model 224 may be generated by creating an artificial neural network, such as a convolutional neural network comprising an input layer of nodes, one or more intermediate layers, and an output layer of nodes. Connections between nodes may be created via the process of "training" the network, in which elements from a training data 204 set are applied to the input nodes, a suitable training algorithm (such as Levenberg-Marquardt, conjugate gradient, simulated annealing, or other algorithms) is then used to adjust the connections and weights between nodes in adjacent layers of the neural network to produce the desired values at the output nodes. This process is sometimes referred to as deep learning.

Still referring to FIG. 2A, machine-learning algorithms may include at least a supervised machine-learning process 228. At least a supervised machine-learning process 228, as defined herein, include algorithms that receive a training set relating a number of inputs to a number of outputs, and seek to find one or more mathematical relations relating inputs to outputs, where each of the one or more mathematical relations is optimal according to some criterion specified to the algorithm using some scoring function. For instance, a supervised learning algorithm may include as described above as inputs, as described above outputs, and a scoring function representing a desired form of relationship to be detected between inputs and outputs; scoring function may, for instance, seek to maximize the probability that a given input and/or combination of elements inputs is associated with a given output to minimize the probability that a given input is not associated with a given output. Scoring function may be expressed as a risk function representing an "expected loss" of an algorithm relating inputs to outputs, where loss is computed as an error function representing a degree to which a prediction generated by the relation is incorrect when compared to a given input-output pair provided in training data 204. Persons skilled in the art, upon reviewing the entirety of this disclosure, will be aware of various possible variations of at least a supervised machine-learning process 228 that may be used to determine relation between inputs and outputs. Supervised machine-learning processes may include classification algorithms as defined above.

Further referring to FIG. 2A, machine learning processes may include at least an unsupervised machine-learning processes 232. An unsupervised machine-learning process, as used herein, is a process that derives inferences in datasets without regard to labels; as a result, an unsupervised machine-learning process may be free to discover any structure, relationship, and/or correlation provided in the data. Unsupervised processes may not require a response variable; unsupervised processes may be used to find interesting patterns and/or inferences between variables, to determine a degree of correlation between two or more variables, or the like.

Still referring to FIG. 2A, machine-learning module 200 may be designed and configured to create a machine-learning model 224 using techniques for development of linear regression models. Linear regression models may include ordinary least squares regression, which aims to minimize the square of the difference between predicted outcomes and actual outcomes according to an appropriate norm for measuring such a difference (e.g., a vector-space distance norm); coefficients of the resulting linear equation may be modified to improve minimization. Linear regression models may include ridge regression methods, where the function to be minimized includes the least-squares function plus term multiplying the square of each coefficient by a scalar amount to penalize large coefficients. Linear regression models may include least absolute shrinkage and selection operator (LASSO) models, in which ridge regression is combined with multiplying the least-squares term by a factor of 1 divided by double the number of samples. Linear regression models may include a multi-task lasso model wherein the norm applied in the least-squares term of the lasso model is the Frobenius norm amounting to the square root of the sum of squares of all terms. Linear regression models may include the elastic net model, a multi-task elastic net model, a least angle regression model, a LARS lasso model, an orthogonal matching pursuit model, a Bayesian regression model, a logistic regression model, a stochastic gradient descent model, a perceptron model, a passive aggressive algorithm, a robustness regression model, a Huber regression model, or any other suitable model that may occur to persons skilled in the art upon reviewing the entirety of this disclosure. Linear regression models may be generalized in an embodiment to polynomial regression models, whereby a polynomial equation (e.g. a quadratic, cubic or higher-order equation) providing a best predicted output/actual output fit is sought; similar methods to those described above may be applied to minimize error functions, as will be apparent to persons skilled in the art upon reviewing the entirety of this disclosure.

Continuing to refer to FIG. 2A, machine-learning algorithms may include, without limitation, linear discriminant analysis. Machine-learning algorithm may include quadratic discriminate analysis. Machine-learning algorithms may include kernel ridge regression. Machine-learning algorithms may include support vector machines, including without limitation support vector classification-based regression processes. Machine-learning algorithms may include stochastic gradient descent algorithms, including classification and regression algorithms based on stochastic gradient descent. Machine-learning algorithms may include nearest neighbors algorithms. Machine-learning algorithms may include various forms of latent space regularization such as variational regularization. Machine-learning algorithms may include Gaussian processes such as Gaussian Process Regression. Machine-learning algorithms may include cross-decomposition algorithms, including partial least squares and/or canonical correlation analysis. Machine-learning algorithms may include naïve Bayes methods. Machine-learning algorithms may include algorithms based on decision trees, such as decision tree classification or regression algorithms. Machine-learning algorithms may include ensemble methods such as bagging meta-estimator, forest of randomized tress, AdaBoost, gradient tree boosting, and/or voting classifier methods. Machine-learning algorithms may include neural net algorithms, including convolutional neural net processes.

Referring now to FIG. 2B, an exemplary table 236 of training data 204. Training data 204 may include any data described throughout this disclosure. For example, training data 204 may contain de-identified user information. A user may be referred to as a patient in this disclosure. De-identified patient information may include patient Age, patient BMI, number of COCs retrieved, AMH Levels (ug/L), antral follicle count (AFC) at last ultrasound, patient oocyte retrieval day E2 Levels (ng/L), patient oocyte retrieval day P4 Levels (ng/L), patient oocyte retrieval day LH (IU/L), patient oocyte retrieval day FSH (IU/L), days of stimulation, gonadotropin used, total injected dose (IU), and the like. Additionally or alternatively, training data 204 may include pre-culture group COC images, post-culture group COC images, post-culture denuded oocyte images, third party notes such as embryologist notes, machine-learning feedback, follicular dynamics information, study sample sheet, frozen oocyte cell lysate data, frozen granulosa cells lysate data, frozen cell culture media data, data from systemic hormone index, data from oocyte analytical index, data from biological sample database 124, data from culture database 144, and the like.

Figure 3:
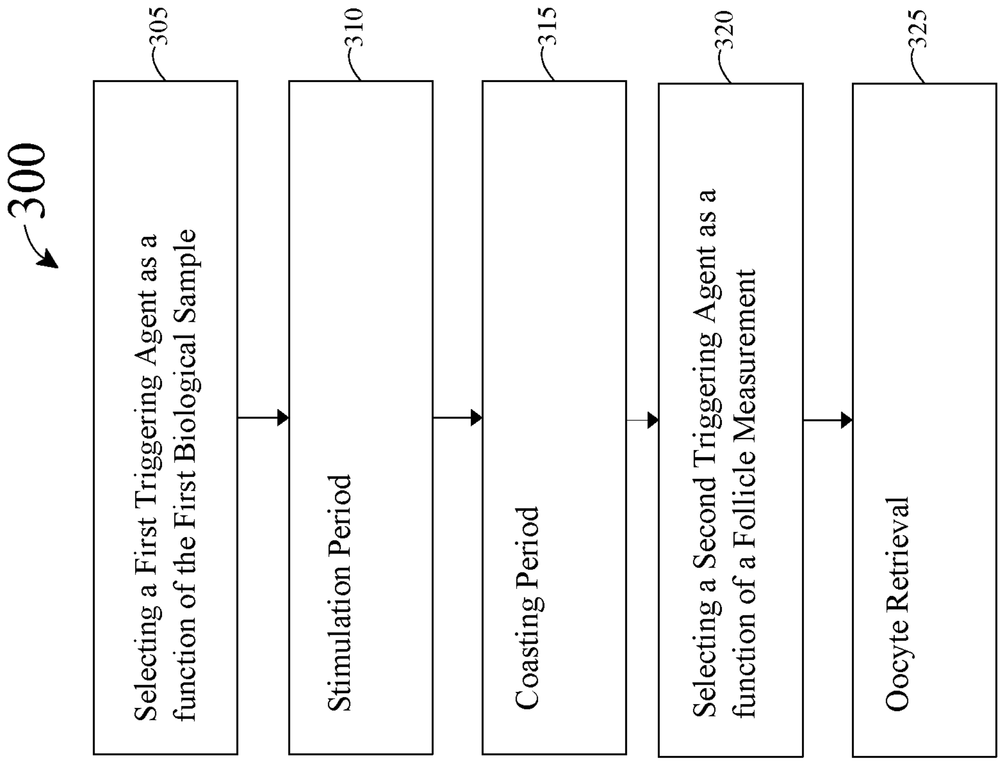
FIG. 3 is an exemplary flow-chart of a mini stimulation protocol.

Referring now to FIG. 3, is an exemplary flow chart of a mini stimulation protocol 300. At step 305, minimal stimulation protocol may include selecting a first triggering agent as a function of the first biological sample to inject a user with. The selected first triggering agent may be selected based on the measured hormone levels of the user. The first triggering agent may include a human recombinant follicle stimulating hormone (rFSH). A rFSH triggering agent may include for example, Gonal-F as produced by Merck Global, Follistim as produced by Merck Global; Follitropin Alfa as produced by Teva, headquartered in Tel Aviv-Yafo, Israel; and Glucophage as produced by Merck Global. rFSH, or any other triggering agent as described throughout this disclosure, may be injected into the user at different increments a plurality of times. In an embodiment, timing as to when minimal stimulation may be initiated by a patient may be determined by a patient's contraception status as described above in more detail. For example, a patient who is not taking contraception may begin stimulation with rFSH on the second day of the patient's menstrual cycle. In yet another non-limiting example, a patient who is taking contraception such as a combined oral contraception (COC) pill may begin stimulation 5 days after the last pill was consumed. Drug dosage and selection may be determined by one or more lab tests such as a blood test taken on the second day of a patient's menstrual cycle to determine blood levels of E2, FSH, LH, p4, and/or AMH. One or more measurements may be utilized to determine ovarian reserve health, circulating hormone levels, and/or fertility status.

At step 310, protocol 300 may include stimulating the user over the span of a time period such as 3 days with the first triggering agent. For example, rFSH may injected in an amount of 100-200IU three or more times over the span of a 1-4-day stimulation period. For example, the stimulation period may span over 3 days. After injection of the first triggering agent an ultrasound may be performed to determine an average follicle size of the cell, such as an oocyte cell. At step 315, protocol may include a day coasting period. A coasting period includes any coasting period as described above as described in more detail. A coasting period may include where a second triggering agent is withheld until serum estradiol (E2) has decreased to what is considered to be, by one skilled in the art, a safe level to prevent the onset of ovarian hyperstimulation syndrome. In some embodiments, an ultrasound may be performed after the 3-day miniature stimulation protocol 300 during a coasting period in order to determine the average follicle size of the cell. In some embodiments, the coasting period may span over 2 days. Determining the average follicle size of the cell may include identifying when the average follicle size is between 8-12 nm. At step 320, as a function of determining the average follicle size of the cell, a second triggering agent may be injected into the user. The second triggering agent may include a human chorionic gonadotropin (hCG). The second triggering agent may be dosed based on one or more factors pertaining to the user including follicle size, previous diagnosis of any medical condition, ultrasound imaging, drug allergy, patient tolerance of a particular medication and the like. A rFSH triggering agent may include for example, Pregnyl as produced by Schering Plough, headquartered in Kenilworth, NJ; Novarel as produced by Ferring Laboratories, headquartered in Parsippany, NJ; Chorex as produced by Encocam, headquartered in Huntingdon, England; and Profasi as produced by Serum Institute of India Ltd, headquartered in Pune, India. In some embodiments, the second triggering may be any triggering agent as described throughout this disclosure. Similar to the first triggering agent, the second triggering agent may be injected into the user at different increments a plurality of times. For example, in an amount ranging from 200 ug-700 ug, injected once or a plurality of times over the span of the 3-day stimulation period. At step 325, after the injection of the second triggering agent, a cell may be retrieved for the user, wherein the cell includes an oocyte cell and/or a COC. For example, after the coasting period, at 8-9 mm follicle size, a 500ug hCG trigger agent may be administered, with oocyte retrieval at 36 hours post-administration. Oocyte retrieval may include a medical professional, such as a doctor inserting the extraction device into the follicle containing an egg and extracting the egg and surrounding fluid. Oocyte retrieval may include retrieval of immature oocytes, mature oocytes, COCs, and any other type of cell involved in reproduction found in the ovaries. Oocyte retrieval may occur during a time frame from anywhere ranging from 12-96 hours after HcG administration. In an embodiment, a blood test to examine levels of hormones such as E2, LH, and/or P4 may be measured to ensure for one or more quality metrics and to check that a patient took the HcG as prescribed. This may also aid in determining if hormone levels are within standard predicted value ranges.

Referring now to FIG. 4, is a table 400 of exemplary metabolite formulations that may be included in a group culture. Metabolite 404 column lists exemplary metabolites that may be use as a triggering agent and/or cell culture metabolites. A "cell culture metabolite," as used in this disclosure, is a substance involved in cell metabolism that optimize the synthesis of new molecules in a cell culture. Stock Solution Preparation Concentration 408 column lists exemplary concentrations for cell culture metabolites. Final Concentration in IVM Media 412 column list exemplary concentrations of cell culture metabolites in a IVM media for group culturing of second biological sample 136. For examples, 10 mg/ml of HSA may be added to an IVM media for group culturing. 75 mIU/ml of FSH may be added to an IVM media for group culturing. 100 mIU/ml of hCG may be added to an IVM media for group culturing. 500 ng/ml of androstenedione may be added to an IVM media for group culturing. 1 ug/ml of doxycycline may be added to an IVM media for group culturing. In some embodiments, steroidogenic granulosa cells, derived from human induced pluripotent stem cells (hiPSCs), may be co-cultured with immature oocytes (COCs), thereby reconstituting the follicular niche in vitro to promote rapid and efficient oocyte maturation in a manner that reinforces oocyte health and developmental competence. As used in this disclosure, a "steroidogenic granulosa cell" is a granulosa cell expressing high levels of steroidogenic enzymes, such as estradiol. For example, a steroidogenic granulosa cell may be a mural granulosa cell extracted from the antral follicle. Applying steroidogenic granulosa cells in the co-cultures of COCs may increase oocyte maturation in vitro after egg/oocyte retrieval, allowing for utilization of all retrieved eggs/oocyte by directly supplying nutrients, raw materials, and mechanical support to oocytes throughout gametogenesis and folliculogenesis. Steroidogenic granulosa cells may grow and perform oocyte maturation of immature COCs in standard IVF and IVM media as described further below. This may increase the overall pool of available, healthy oocytes for use in IVF and reduce the number of egg/oocyte retrieval procedures a user is subjected to.

Figure 5:
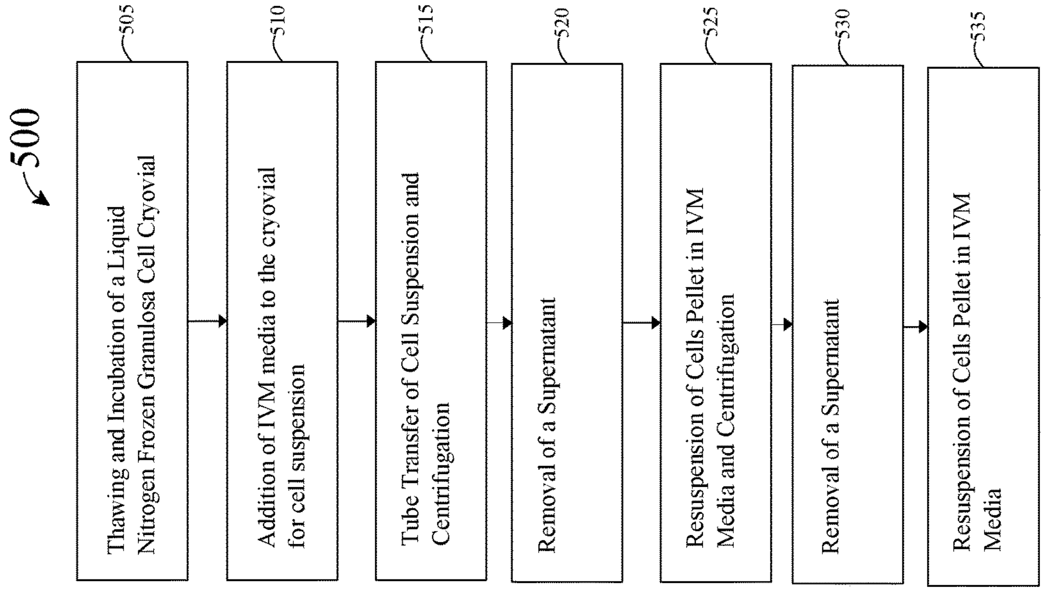
FIG. 5 is an exemplary flow-chart for preparing a granulosa co-culture.

Referring now to FIG. 5, is an exemplary flow-chart 500 for preparing a granulosa co-culture is illustrated. Granulosa cells in a woman's ovaries play a key role in the female reproductive system. These cells release estrogen, progesterone and other hormones which drive oocyte maturation in the ovary, making them a logical tool for application in IVM. Furthermore, granulosa cells provide the developmental niche for follicle and oocyte development, directly supplying nutrients, raw materials, and mechanical support to oocytes throughout gametogenesis and folliculogenesis. At step 505, a liquid nitrogen frozen granulosa cell cryovial may be thawed and incubated. The granulosa cell cryovial may be a ImL cryovial containing 100,000 granulosa cells. Thawing may occur by placing the granulosa cell cryovial in a water bath od a dry bead bath. The granulosa cell cryovial may be incubated for 3 to 5 minutes. At step 510, IVM media may be added to the cryovial for cell suspension. In some embodiments, 0.5 ml of ICM media may be added to induce cell suspension. At step 515, the cell suspension is transferred to a tube and centrifuged. In some embodiments, 1 mL of cell suspension may be transferred to a 1.5 mL tube, wherein the tube is centrifuged at 300×g for 5 minutes. At step 520, a pipette may be used to remove a supernatant. Pipette may be a p1000 pipette. At step 525, cells pellet formed as a function of centrifuged tube containing the cell suspension, may be resuspended in a IVM media and centrifuged. IVM media may be a 1 mL IVM media. The tube may be centrifuged as described above. At step 530, a pipette may be used to remove a supernatant. Pipette may be a p1000 pipette. At step 535 cells pellet may be resuspend in a IVM media. IVM media may be a 0.1 mL IVM media. At this step, granulosa cell may now be at 1,00 cells per 1 ul. In some embodiments 10 ul of the cell suspension may be utilized per oocyte in second biological sample 136 related to a user.

Figure 6B:
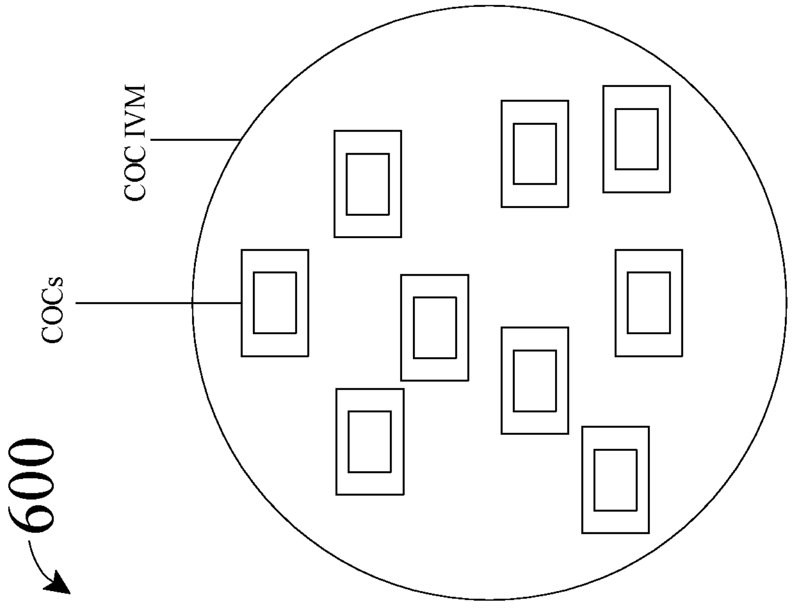
FIG. 6B is an exemplary embodiment of a control group culture of a second biological sample.
Figure 6A:
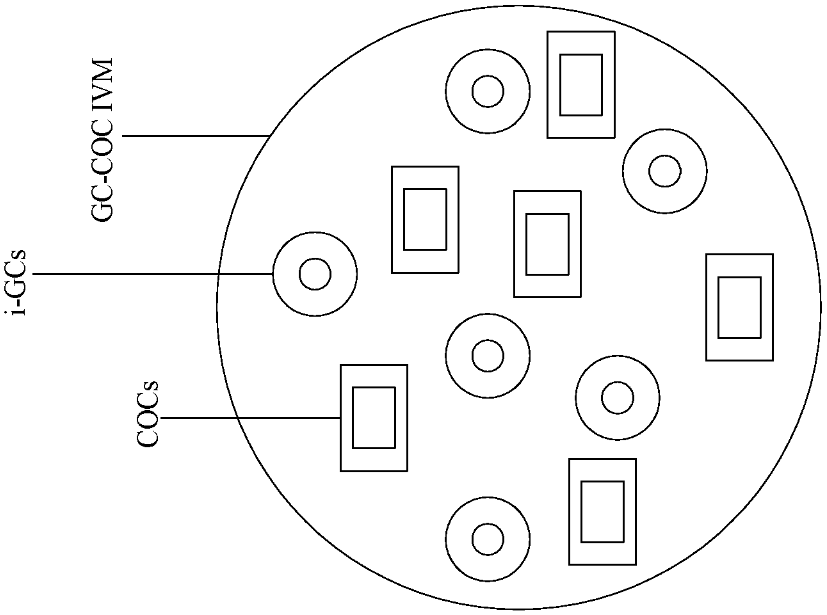
FIG. 6A is an exemplary embodiment of a co-cultured second biological sample.

Referring now to FIG. 6A, is an exemplary embodiment 600 of a co-cultured second biological sample 136 including immature COCs related to the user. In some embodiments, COCs received after oocyte retrieval from a follicular aspirate relating to the user may be randomly divided in half to into a media, such as a Lag media of a granulosa cell plate, and the other half may go into a LAG media of a no-co-culture plate. COCs may be incubated in the LAG media at 37C for 2 hours. Granulosa cells may be prepared as described in FIG.5. The prepared granulosa cells may be added to the right center well that contain IVM media, adding 10,000 granulosa cells per COC that may be cultured. The dish with the granulosa cell may then be placed back in the incubator until use. After the 2-hour incubation period, the COCs in the LAG media may be transferred to the IVM media in the granulosa cell dish with a Pasteur pipette.

Referring now to FIG. 6B, is an exemplary embodiment 600 of a control group culture of second biological sample 136 including immature COCs related to the user. COCs may be incubated in a LAG media at 37C for 2 hours. After the 2-hour incubation period, the COCs in the LAG media may be transferred to a IVM media in a control dish with a Pasteur pipette.

Figure 7:
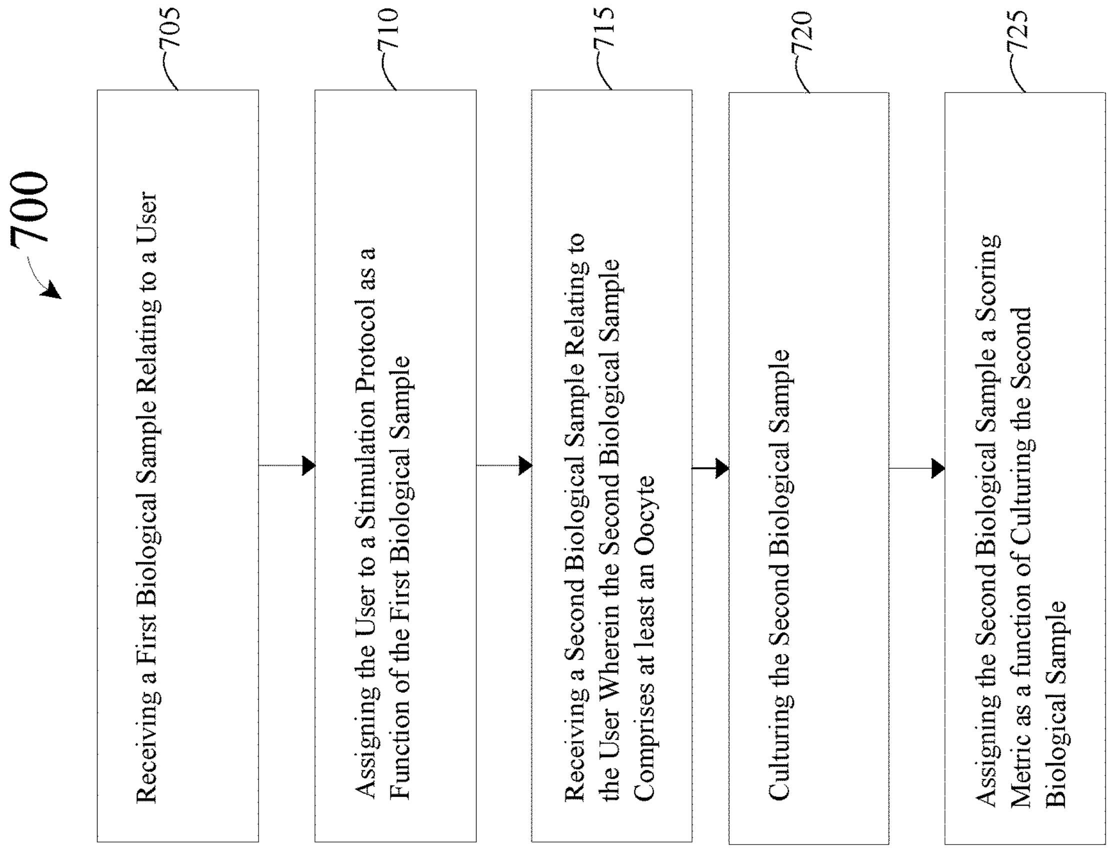
FIG. 7 is a flow diagram of an exemplary method for inducing human oocyte maturation in vitro.

Referring now to FIG. 7, is a flow diagram of an exemplary method for inducing human oocyte maturation in vitro. Method 700 may include using computing device 104 to carry out steps to be listed. At step 705, method 700 includes receiving a first biological sample relating to a user. The first biological sample may be any form of biological sample as defined and exemplified throughout this this disclosure. For example, the first biological sample may include a blood sample from a user as exemplified, at least, in FIG. 1. A user may be a user as defined in FIG. 1, such as a person. In some embodiments, the biological sample may be extracted from the user through an extraction device, as defined and exemplified, at least, in FIG. 1. For example, the extraction device may include a medical syringe to draw blood from the user. Biological samples may also include systemic hormones. At step 710, method 700 includes assigning the user to a stimulation protocol as a function of the first biological sample. A stimulation protocol is a medication injection process as defined and exemplified, at least, in FIG. 1. In some embodiments, the stimulation protocol may be assigned based on a measured hormone level of the biological sample. The measured hormone level, as defined in FIG. 1, may include E2, LH, FSH, and/or P4 levels. The assigned stimulation protocol may include a minimal stimulation protocol configured to trigger the release of a cell in the span of 3 days as defined and exemplified, at least, in FIG. 1. In an embodiment, the minimal stimulation protocol may include selecting a first triggering agent as a function of the first biological sample and selecting a second triggering agent as a function of a follicle measurement. A triggering agent, as defined in FIG. 1, may include human Serum Albumin, FSH, hCG, androstenedione, and doxycycline in formulation described in FIGS. 1-6 in this disclosure.

Still referring to step 710, in some embodiments, the minimal stimulation protocol may include injecting a user with a first triggering agent; performing an ultrasound to determine an average follicle size of the cell; injecting the user with a second triggering agent; and retrieving the cell, wherein the cell includes an oocyte cell from the user. The first triggering agent may include a human recombinant follicle stimulating hormone (rFSH). rFSH may be injected into the user at different increments a plurality of times. For example, and with reference to FIG. 1, rFSH may be injected in an amount of 100-200IU three or more times over the span of a 3-day stimulation period. After injection of the first triggering agent an ultrasound may be performed to determine an average follicle size of the cell, such as an oocyte cell. In some embodiments, the ultrasound may be performed, after the 3-day stimulation protocol, during a 2-day coasting period, as defined in FIG. 1. Determining the average follicle of the cell may include identifying when the average follicle size is between 8-12 nm. As function of determining the average follicle size of the cell, a second triggering agent may be injected into the user. The second triggering agent may include a human chorionic gonadotropin (hCG). Similar to the first triggering agent, the second triggering agent may be injected into the user at different increments a plurality of times. For example, and with reference to FIG. 1, the second triggering agent may in an amount ranging from 200ug-700ug, injected once or a plurality of times over the span of the 3-day stimulation period. After the injection of the second triggering agent, a cell may be retrieved for the user, wherein the cell includes and oocyte cell. For example, and with reference to FIG. 1, after the coasting period, at 8-9 mm follicle size, a 500ug hCG trigger may be administered, with oocyte retrieval at 36 hours post-administration. Oocyte retrieval may include a medical professional, such as a doctor inserting the extraction device into the follicle containing an egg and extracting the and surrounding fluid.

Still referring to FIG. 7, method 700 at step 715, includes receiving a second biological sample relating to the user wherein the second biological sample includes at least an immature Cumulus-Oocyte complex (COCs) as define din FIG. 1. The second biological sample may include bodily fluids as described above. The second biological sample may be extracted using an extraction device and received as disclosed above. At step 720, method 700 includes culturing the second biological sample. In some embodiments, culturing the second biological sample may include culturing the Cumulus-Oocyte complexes in a group culture, as defined in FIG. 1. For example, and with reference to FIGS. 1-6, group culturing may include culturing the Cumulus-Oocyte complexes with a granulosa co-culture and a control group of COCs with no co-culture. In some embodiments cell culture media may include LAG media. For example, and with reference to FIGS. 1-6, LAG media may be used for the incubation of COCs post-retrieval from the stimulation protocol. Package size may be a 10 ml vial. Storage may be at 2-8° C. away from light up to one month. Media equilibration may be 18 to 24 hours pre-culture, include a seed 100 ul droplet and placed into 37C incubator with 6% O2 and proper CO2. In some embodiments, cell culture media may include IVM media. For example, and with reference to FIGS. 1-6, a modified-MediCult IVM media may be used a baseline control during the culturing process. Package size may be a 10 ml vial. Storage may be at 2-8° C. away from light up to one month. In some embodiments, the cell culture mediums may include metabolites. For example, the modified-MediCult IVM media may include human serum albumin, FSH, hCG, androstenedione, doxycycline and other compounds. Other cell culture material and equipment may include: liquid nitrogen, hyaluronidase, dPBS, IVF-Qualified mineral oil, universal GPS dishes, G-NOPS plus media, micropipettes, stripper pipettors, camera-equipped inverted ICSI Microscope, Dry Inject Tabletop incubators, saturated humidity incubators, EmbryoScope, microcentrifuge, 4° ° C. refrigerator, −20° C. freezer, −80° C. freezer, liquid nitrogen storage dewer, 35 mm dishes for denuding, stripper pipette tips, and other components one skilled in the art would understand to be included in the cell culture process.

Still referring to FIG. 7, at step 725, method 700 includes assigning the second biological sample a scoring metric as a function of culturing the second biological sample. Assignment may be based patient information regarding the completion of the stimulation protocol such as: patient Age, patient BMI, number of COCs retrieved, AMH Levels (ug/L), antral follicle count (AFC) at last ultrasound, patient oocyte retrieval day E2 Levels (ng/L), patient oocyte retrieval day P4 Levels (ng/L), patient oocyte retrieval day LH (IU/L), patient oocyte retrieval day FSH (IU/L), Days of stimulation, Gonadotropin used, and total injected dose (IU). In some embodiments, assignment of the scoring metric may include imaging the group cultures and analyzing the images of one or both of co-culture and no-co-culture growth groups. For example. Group culture images may contain a pre-culture group COC image, a post-culture group COC image, and a post-culture denuded oocyte image. In some embodiments, images may be sent to a third party, as define din FIG. 1, for scoring assignment. In some embodiments the scoring metric 152 may include total oocyte scoring (TOS) as a function of analyzing the imaged group cultures. Oocyte scoring may include metrics such as shape, size, ooplasm characteristics, structure of the perivitelline space (PVS), zona pellucida (ZP), polar body (PB) morphology, and the like as described in detail at least in FIG. 1. Total oocyte scoring on both pre and post culture oocyte images for generation of the TOS metric may be based on a scale system of −6 to +6.

In some embodiments, the scoring metric may include performing an outcome analysis as a function of the TOS as defined and exemplified in FIG. 1. Parametric or non-parametric tests may be applied to determine the significance of findings during the analysis. Outcome analysis may be used to determine GV to MII oocyte maturation rate; GV to MI oocyte maturation rate; MI to MII oocyte maturation rate; Average Total Oocyte Score; Average Oocyte Shape; Average Oocyte Size; Average Ooplasm quality; Average PVS quality; Average ZP quality; Average Polar Body quality, and the like. In some embodiments these outcomes may reported as a as mean, median, and deviation.

Still referring to step 725, in some embodiments, the scoring metric may include an Omics-based analysis. For example, and with reference to FIG. 1, frozen cell lysates and cell culture mediums may be analyzed for bulk RNA-sequencing, whole genome bisulfite sequencing (WGBS), mass spectrometry-based proteomics and metabolomics. Cell culture media may be utilized for metabolomics analysis to determine changes in molecular content of media following co-culture compared to pre-culture media controls. This may be utilized to profile dynamic changes in paracrine signaling between granulosa cells and oocytes. The data gathered may then be aggregated for downstream analysis for determination of changes in epigenetic state, metabolite presence, and gene expression between different co-culture conditions and controls.

It is to be noted that any one or more of the aspects and embodiments described herein may be conveniently implemented using one or more machines (e.g., one or more computing devices that are utilized as a user computing device for an electronic document, one or more server devices, such as a document server, etc.) programmed according to the teachings of the present specification, as will be apparent to those of ordinary skill in the computer art. Appropriate software coding can readily be prepared by skilled programmers based on the teachings of the present disclosure, as will be apparent to those of ordinary skill in the software art. Aspects and implementations discussed above employing software and/or software modules may also include appropriate hardware for assisting in the implementation of the machine executable instructions of the software and/or software module.

Such software may be a computer program product that employs a machine-readable storage medium. A machine-readable storage medium may be any medium that is capable of storing and/or encoding a sequence of instructions for execution by a machine (e.g., a computing device) and that causes the machine to perform any one of the methodologies and/or embodiments described herein. Examples of a machine-readable storage medium include, but are not limited to, a magnetic disk, an optical disc (e.g., CD, CD-R, DVD, DVD-R, etc.), a magneto-optical disk, a read-only memory "ROM" device, a random access memory "RAM" device, a magnetic card, an optical card, a solid-state memory device, an EPROM, an EEPROM, and any combinations thereof. A machine-readable medium, as used herein, is intended to include a single medium as well as a collection of physically separate media, such as, for example, a collection of compact discs or one or more hard disk drives in combination with a computer memory. As used herein, a machine-readable storage medium does not include transitory forms of signal transmission.

Such software may also include information (e.g., data) carried as a data signal on a data carrier, such as a carrier wave. For example, machine-executable information may be included as a data-carrying signal embodied in a data carrier in which the signal encodes a sequence of instruction, or portion thereof, for execution by a machine (e.g., a computing device) and any related information (e.g., data structures and data) that causes the machine to perform any one of the methodologies and/or embodiments described herein.

Examples of a computing device include, but are not limited to, an electronic book reading device, a computer workstation, a terminal computer, a server computer, a handheld device (e.g., a tablet computer, a smartphone, etc.), a web appliance, a network router, a network switch, a network bridge, any machine capable of executing a sequence of instructions that specify an action to be taken by that machine, and any combinations thereof. In one example, a computing device may include and/or be included in a kiosk.

Figure 8:
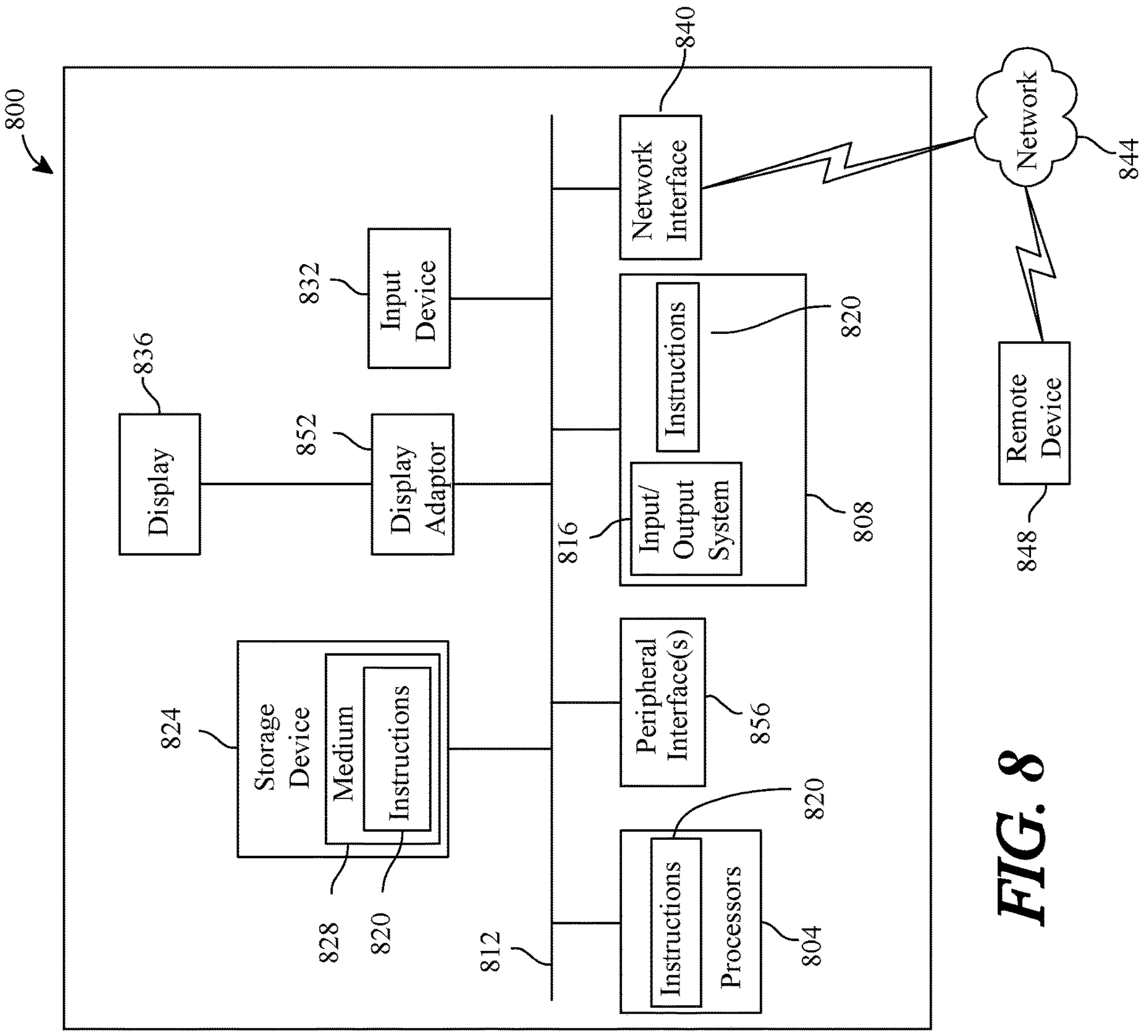
FIG. 8 is a block diagram of a computing system that can be used to implement any one or more of the methodologies disclosed herein and any one or more portions thereof.

FIG. 8 shows a diagrammatic representation of one embodiment of a computing device in the exemplary form of a computer system 800 within which a set of instructions for causing a control system to perform any one or more of the aspects and/or methodologies of the present disclosure may be executed. It is also contemplated that multiple computing devices may be utilized to implement a specially configured set of instructions for causing one or more of the devices to perform any one or more of the aspects and/or methodologies of the present disclosure. Computer system 800 includes a processor 804 and a memory 808 that communicate with each other, and with other components, via a bus 812. Bus 812 may include any of several types of bus structures including, but not limited to, a memory bus, a memory controller, a peripheral bus, a local bus, and any combinations thereof, using any of a variety of bus architectures.

Processor 804 may include any suitable processor, such as without limitation a processor incorporating logical circuitry for performing arithmetic and logical operations, such as an arithmetic and logic unit (ALU), which may be regulated with a state machine and directed by operational inputs from memory and/or sensors; processor 804 may be organized according to Von Neumann and/or Harvard architecture as a non-limiting example. Processor 804 may include, incorporate, and/or be incorporated in, without limitation, a microcontroller, microprocessor, digital signal processor (DSP), Field Programmable Gate Array (FPGA), Complex Programmable Logic Device (CPLD), Graphical Processing Unit (GPU), general purpose GPU, Tensor Processing Unit (TPU), analog or mixed signal processor, Trusted Platform Module (TPM), a floating point unit (FPU), and/or system on a chip (SoC).

Memory 808 may include various components (e.g., machine-readable media) including, but not limited to, a random-access memory component, a read only component, and any combinations thereof. In one example, a basic input/output system 816 (BIOS), including basic routines that help to transfer information between elements within computer system 800, such as during start-up, may be stored in memory 808. Memory 808 may also include (e.g., stored on one or more machine-readable media) instructions (e.g., software) 820 embodying any one or more of the aspects and/or methodologies of the present disclosure. In another example, memory 808 may further include any number of program modules including, but not limited to, an operating system, one or more application programs, other program modules, program data, and any combinations thereof.

Computer system 800 may also include a storage device 824. Examples of a storage device (e.g., storage device 824) include, but are not limited to, a hard disk drive, a magnetic disk drive, an optical disc drive in combination with an optical medium, a solid-state memory device, and any combinations thereof. Storage device 824 may be connected to bus 812 by an appropriate interface (not shown). Example interfaces include, but are not limited to, SCSI, advanced technology attachment (ATA), serial ATA, universal serial bus (USB), IEEE 1394 (FIREWIRE), and any combinations thereof. In one example, storage device 824 (or one or more components thereof) may be removably interfaced with computer system 800 (e.g., via an external port connector (not shown)). Particularly, storage device 824 and an associated machine-readable medium 828 may provide nonvolatile and/or volatile storage of machine-readable instructions, data structures, program modules, and/or other data for computer system 800. In one example, software 820 may reside, completely or partially, within machine-readable medium 828. In another example, software 820 may reside, completely or partially, within processor 804.

Computer system 800 may also include an input device 832. In one example, a user of computer system 800 may enter commands and/or other information into computer system 800 via input device 832. Examples of an input device 832 include, but are not limited to, an alpha-numeric input device (e.g., a keyboard), a pointing device, a joystick, a gamepad, an audio input device (e.g., a microphone, a voice response system, etc.), a cursor control device (e.g., a mouse), a touchpad, an optical scanner, a video capture device (e.g., a still camera, a video camera), a touchscreen, and any combinations thereof. Input device 832 may be interfaced to bus 812 via any of a variety of interfaces (not shown) including, but not limited to, a serial interface, a parallel interface, a game port, a USB interface, a FIREWIRE interface, a direct interface to bus 812, and any combinations thereof. Input device 832 may include a touch screen interface that may be a part of or separate from display 836, discussed further below. Input device 832 may be utilized as a user selection device for selecting one or more graphical representations in a graphical interface as described above.

A user may also input commands and/or other information to computer system 800 via storage device 824 (e.g., a removable disk drive, a flash drive, etc.) and/or network interface device 840. A network interface device, such as network interface device 840, may be utilized for connecting computer system 800 to one or more of a variety of networks, such as network 844, and one or more remote devices 848 connected thereto. Examples of a network interface device include, but are not limited to, a network interface card (e.g., a mobile network interface card, a LAN card), a modem, and any combination thereof. Examples of a network include, but are not limited to, a wide area network (e.g., the Internet, an enterprise network), a local area network (e.g., a network associated with an office, a building, a campus or other relatively small geographic space), a telephone network, a data network associated with a telephone/voice provider (e.g., a mobile communications provider data and/or voice network), a direct connection between two computing devices, and any combinations thereof. A network, such as network 844, may employ a wired and/or a wireless mode of communication. In general, any network topology may be used. Information (e.g., data, software 820, etc.) may be communicated to and/or from computer system 800 via network interface device 840.

Computer system 800 may further include a video display adapter 852 for communicating a displayable image to a display device, such as display device 836. Examples of a display device include, but are not limited to, a liquid crystal display (LCD), a cathode ray tube (CRT), a plasma display, a light emitting diode (LED) display, and any combinations thereof. Display adapter 852 and display device 836 may be utilized in combination with processor 804 to provide graphical representations of aspects of the present disclosure. In addition to a display device, computer system 800 may include one or more other peripheral output devices including, but not limited to, an audio speaker, a printer, and any combinations thereof. Such peripheral output devices may be connected to bus 812 via a peripheral interface 856. Examples of a peripheral interface include, but are not limited to, a serial port, a USB connection, a FIREWIRE connection, a parallel connection, and any combinations thereof.

The foregoing has been a detailed description of illustrative embodiments of the invention. Various modifications and additions can be made without departing from the spirit and scope of this invention. Features of each of the various embodiments described above may be combined with features of other described embodiments as appropriate in order to provide a multiplicity of feature combinations in associated new embodiments. Furthermore, while the foregoing describes a number of separate embodiments, what has been described herein is merely illustrative of the application of the principles of the present invention. Additionally, although particular methods herein may be illustrated and/or described as being performed in a specific order, the ordering is highly variable within ordinary skill to achieve methods, apparatuses, systems, and software according to the present disclosure. Accordingly, this description is meant to be taken only by way of example, and not to otherwise limit the scope of this invention.

Exemplary embodiments have been disclosed above and illustrated in the accompanying drawings. It will be understood by those skilled in the art that various changes, omissions and additions may be made to that which is specifically disclosed herein without departing from the spirit and scope of the present invention.

What is claimed is:

1. A method of maturing one or more immature oocytes from a human subject for use in an assisted reproduction technology (ART) procedure, the method comprising:

(i) retrieving one or more immature oocytes from the subject; and (ii) co-culturing the one or more immature oocytes with a population of granulosa cells generated from one or more exogenous stem cells;

wherein the one or more exogenous stem cells are human induced pluripotent stem cells (hiPSCs), thereby maturing the one or more oocytes.

2. The method of claim 1, wherein prior to retrieval of the one or more oocytes from the subject, the subject is administered one or more follicular stimulation agents during a follicular stimulation period.

3. A method of producing a mature oocyte for use in an ART procedure, the method comprising co-culturing one or more immature oocytes that have previously been retrieved from a human subject with a population of granulosa cells generated from one or more exogenous stem cells, wherein the one or more exogenous stem cells are hiPSCs, thereby maturing the one or more oocytes.

4. The method of claim 3, wherein the one or more immature oocytes retrieved from the subject comprise one or more germinal vesicle (GV)-stage or metaphase I (MI)-stage oocytes.

5. The method of claim 3, wherein the granulosa cells comprise steroidogenic granulosa cells, optionally wherein the steroidogenic granulosa cells produce estradiol.

6. The method of claim 3, wherein the population of granulosa cells comprises from about 50,000 to about 500,000 granulosa cells.

7. The method of claim 3, wherein the one or more oocytes are co- cultured with the population of granulosa cells in the presence of one or more of human serum albumin, FSH, hCG, and androstenedione.

8. The method of claim 7, wherein the one or more oocytes are co- cultured with the population of granulosa cells in the presence of:

(a) 10 mg/ml of human serum albumin;
(b) 75 mlU/ml of FSH;
(c) 100 mlU/ml of hCG; and/or
(d) 500 ng/ml of androstenedione.

9. The method of claim 3, wherein the one or more oocytes are denuded following co-culturing.

10. The method of claim 3, wherein prior to retrieval of the one or more oocytes from the subject, the subject is administered one or more follicular stimulation agents during a follicular stimulation period.

11. The method of claim 10, wherein the one or more follicular stimulation agents comprise follicle stimulating hormone (FSH).

12. The method of claim 11, wherein the FSH is administered to the subject once daily.

13. The method of claim 12, wherein the FSH is administered to the subject in a plurality of doses over the span of the follicular stimulation period, wherein each of the doses comprises from about 100 international units (IU) to about 200 IU of the FSH.

14. The method of claim 12, wherein the FSH is administered to the subject in an amount of from about 300 IU to about 600 IU per day, from about 300 IU to about 500 IU per day, or from about 300 IU to about 400 IU per day.

15. The method of claim 10, wherein following the follicular stimulation period, the subject undergoes a coasting period during which time a follicular stimulation agent is not administered to the subject, optionally wherein the coasting period has a duration of from 1 day to 2 days.

16. The method of claim 10, wherein:

(a) the subject is one that has completed oral contraceptive treatment within 28 days of commencement of the follicular stimulation period, and wherein the follicular stimulation period commences at least 5 days after cessation of the contraceptive treatment; or
(b) the subject has not undergone oral contraceptive treatment within 28 days of commencement of the follicular stimulation period, and wherein the follicular stimulation period commences on day 2 of the subject's menstrual cycle.

17. The method of claim 10, wherein the follicular stimulation period has a duration of from 2 days to 5 days.

18. The method of claim 17, wherein the follicular stimulation period has a duration of 2 days.

19. The method of claim 17, wherein the follicular stimulation period has a duration of 3 days.

20. The method of claim 17, wherein the follicular stimulation period has a duration of 4 days.

21. The method of claim 17, wherein the follicular stimulation period has a duration of 5 days.

* * * * *